US011969593B2

(12) United States Patent
Ramírez Aristeguieta et al.

(10) Patent No.: US 11,969,593 B2
(45) Date of Patent: Apr. 30, 2024

(54) SYSTEM FOR THE TREATMENT OF DRY MOUTH USING ELECTRICAL STIMULATION OF THE SALIVARY GLANDS

(71) Applicants: Luis Miguel Ramírez Aristeguieta, Medellín (CO); Ben Zion Beiski, Kiryat-Ono (IL); Diego José Luis Botia Valderrama, Medellín (CO); Andy Wolff, Harutzim (IL); Jonathan Gallego Londoño, Medellín (CO); Luis Gabriel Lafaurie Ponce, Medellín (CO); Juan Felipe Ospina Mejía, Medellín (CO); Daniel Felipe Salazar Ramírez, Medellín (CO)

(72) Inventors: Luis Miguel Ramírez Aristeguieta, Medellín (CO); Ben Zion Beiski, Kiryat-Ono (IL); Diego José Luis Botia Valderrama, Medellín (CO); Andy Wolff, Harutzim (IL); Jonathan Gallego Londoño, Medellín (CO); Luis Gabriel Lafaurie Ponce, Medellín (CO); Juan Felipe Ospina Mejía, Medellín (CO); Daniel Felipe Salazar Ramírez, Medellín (CO)

( * ) Notice: Subject to any disclaimer, the term of this patent is extended or adjusted under 35 U.S.C. 154(b) by 0 days.

(21) Appl. No.: 16/404,135

(22) Filed: May 6, 2019

(65) Prior Publication Data
US 2019/0336762 A1 Nov. 7, 2019

Related U.S. Application Data

(60) Provisional application No. 62/667,523, filed on May 6, 2018.

(51) Int. Cl.
*A61N 1/36* (2006.01)
*A61N 1/04* (2006.01)

(52) U.S. Cl.
CPC ........ *A61N 1/36014* (2013.01); *A61N 1/0456* (2013.01)

(58) Field of Classification Search
CPC .... A61N 1/0456; A61N 1/36014; A61N 1/32; A61N 1/18; A61N 1/3603; A61N 1/36034; A61N 1/36036; A61H 39/002
See application file for complete search history.

(56) References Cited

U.S. PATENT DOCUMENTS 5,512,057 A * 4/1996 Reiss ................. A61N 1/36021
607/62
9,283,111 B2 * 3/2016 Rogers ...................... A61F 7/12
(Continued)

FOREIGN PATENT DOCUMENTS

EP         2198915 A1 *  6/2010  ............... A61N 1/04
WO    WO-0071075 A1 * 11/2000  ............. A61N 1/322

OTHER PUBLICATIONS

Delf, Jonathan. "The Submandibular Gland." TeachMeAnatomy, 2017, teachmeanatomy.info/head/organs/salivary-glands/submandibular/.*
(Continued)

*Primary Examiner* — Nathan J Jenness
*Assistant Examiner* — Skylar Lindsey Christianson
(74) *Attorney, Agent, or Firm* — Dunlap Bennett & Ludwig, PLLC

(57) ABSTRACT

A system for electrical stimulation of the salivary glands for the treatment of dry mouth is disclosed. In one embodiment, the system includes a headset with an electronic control module, placed on the back head, and a stimulating module, placed on the area to be stimulated. Both modules are connected by an elastic arm. The stimulating module provides one or more pairs of electrodes in contact with neuro-sensitive areas of a patient, and is anchored in the ear canal. The position of the electrodes is adjustable for opti- (Continued)

mized stimulation. The system may be operated by control bottoms that are part of the electronic control module or by a mobile device, such as a wireless remote control, a smartphone, or a tablet. A mobile device camera may be used for correcting the placement of the electrodes.

16 Claims, 31 Drawing Sheets

(56) References Cited

U.S. PATENT DOCUMENTS

| | | | | |
|---|---|---|---|---|
| 9,566,432 | B2* | 2/2017 | Wolff | A61N 1/36034 |
| 9,827,418 | B2* | 11/2017 | Southwell | A61N 1/0452 |
| 10,448,889 | B2* | 10/2019 | Gerber | A61N 1/37247 |
| 2002/0094094 | A1* | 7/2002 | Shin | H04R 1/1066 |
| | | | | 381/104 |
| 2013/0012840 | A1* | 1/2013 | Feferberg | A61N 1/18 |
| | | | | 601/2 |
| 2014/0376765 | A1* | 12/2014 | Toelle | H04R 1/1016 |
| | | | | 381/384 |
| 2015/0335876 | A1* | 11/2015 | Jeffery | A61N 1/0492 |
| | | | | 607/139 |
| 2015/0374971 | A1* | 12/2015 | Dar | A61B 5/6803 |
| | | | | 607/139 |
| 2016/0074657 | A1* | 3/2016 | Kwan | A61N 1/36031 |
| | | | | 607/45 |
| 2016/0279024 | A1* | 9/2016 | Hyde | A61H 23/02 |
| 2017/0224990 | A1* | 8/2017 | Goldwasser | A61N 1/0476 |

OTHER PUBLICATIONS

Aggarwal H et al. "Evaluation of the effect of transcutaneous electrical nerve stimulation (TENS) on whole salivary flow rate." J Clin Exp Dent. 2015; 7(1): e13-e17.*

* cited by examiner

| Subject | Gender | Age | VAS Wetness | VAS Comfort |
|---|---|---|---|---|
| 1 | m | 22 | 7 | 8 |
| 2 | f | 18 | 5 | 7 |
| 3 | f | 44 | 8,5 | 10 |
| 4 | m | 23 | 5 | 8 |
| 5 | m | 34 | 3 | 8 |
| 6 | m | 25 | 1 | 6 |

Figure 29

SYSTEM FOR THE TREATMENT OF DRY MOUTH USING ELECTRICAL STIMULATION OF THE SALIVARY GLANDS

CROSS-REFERENCE TO RELATED APPLICATION

This application claims the benefit of priority of U.S. provisional application No. 62/667,523, filed May 6, 2018 the contents of which are herein incorporated by reference.

BACKGROUND OF THE INVENTION

The present invention is generally directed to the treatment of dry mouth, and is more specifically directed to a transcutaneous electrical stimulation device and method for applying a series of electrical pulses to the nerves that control salivary gland function by one or more channels of electrodes in accordance with procedures for treating dry mouth, where control and selection of a specific procedure is done using a mobile device application. The device and method improve symptoms in persons with dry mouth or xerostomia by increasing the salivary flow.

Saliva plays a fundamental role in maintaining oral functionality and oral health. Among its functions are protection of the oral cavity by antibacterial, antiviral and antifungal actions, buffering capacity, re-mineralization, and washing, and facilitating speech and digestion. Salivary gland hypofunction (SGH) is a condition in which non-stimulated or stimulated salivary flow is significantly reduced. Hyposalivation is defined as a salivary flow rate under 0.1-0.2 mL/min (non-stimulated) or 0.7 mL/min (stimulated). Xerostomia (the feeling of dry mouth) is a symptom of hyposalivation. Xerostomia prevalence is approximately 20% among the general population. The major reasons for dry mouth include medication side effects, radiotherapy of the head and neck region, chemotherapy, autoimmune disease (mainly Sjögren's Syndrome), infections, and hormone disorders. Xerostomia prevalence is higher among the older population. Saliva is generated mainly by three pairs of salivary glands; the parotid gland, sublingual gland and mandibular gland (FIG. 1). In addition, there are hundreds and even thousands of minor salivary glands that are scattered on most of the oral cavity tissue.

It is known for over 150 years that the nerves control the secretion of saliva. Saliva secretion is regulated by a three-component reflex arch including: (i) afferent receptors and nerves, (ii) a central connection and processing nucleus (salivation center), and (iii) an efferent reflex arm constituted by parasympathetic and sympathetic nerves bundles.

The afferent nerves carry impulses from the periphery (mainly the oral cavity) to the salivation center in the medulla oblongata, which in turn directs signals to the efferent part of the reflex arch causing salivation.

The electrical stimulation of one of the components of the salivary reflex arch leads to increase of natural saliva secretion. Potential mechanisms of transcutaneous electrical nerve stimulation (TENS) are: stimulation of the nerves associated with the salivary glands (mainly the lingual nerve) and generating evoked potentials, and/or an increase in blood supply and the stimulation of the auriculotemporal nerve, especially at the parotid gland. Application of TENS on acupuncture points has been described, as well. This stimulation consequently increases salivary flow and improves the quality of the saliva. TENS and all its variations, is based on application of relatively low frequency (typically 1 Hz up to 20 KHz), pulsed electrical currents. These electrical currents are transmitted via surface electrode pads placed on the skin surface that stimulate the peripheral nerves to produce various physiological effects.

Transcutaneous electrical nerve stimulation (TENS) has become known worldwide since its first introduction in 1965. Based on the gate control theory by Melzack and Wall, it is considered to be one of the most common therapeutic resources used in clinical practice for the relief of chronic and acute pain. U.S. Pat. Nos. 4,519,400 and 4,637,405 teach a TENS-like device that comprises an electrical probe placed in the mouth, which is connected to an extracorporeal device, to stimulate the salivary glands to produce more saliva. U.S. Pat. 6,230,052 teaches an electro stimulator supported on a dental implant. This device, with built-in microprocessor, stimulating electronic modules and power source, at a size of a tooth crown, is placed on top of a dental implant. A recent study has shown significant increase in salivary flow rates upon application of TENS, by placement of its surface electrode pads externally on the skin, overlying the parotid glands, with minimal or no side effects (Aggarwal H et al. J Clin Exp Dent. 2015; 7(1): e13-e17. Thus, TENS may also be used to increase salivary flow by stimulating the peripheral nerves.

Examples of the types of electrical stimulation that may be similarly used include, but are not limited to, Patterned Electrical Neuromuscular Stimulation (PENS), Neuromuscular Electrical Stimulation (NMES), Interferential Current (IFC), Percutaneous Electrical Muscle Stimulation (PEMS), Percutaneous Electrical Nerve Stimulation (PENS), which may use alternating or modulated alternating current waveforms, asymmetrical or symmetrical biphasic pulsed current waveforms and monophasic pulsed current waveforms. Other types of electrical stimulation may also be used in accordance with the present invention.

As used herein, the term "tissue" refers to an aggregation of cells and associated intercellular matrix acting together to perform one or more specific functions in the body, including epithelial, mucosal, connective, muscle, and neural tissue.

The term "dry mouth" used in the patent is referred to the conditions of hyposalivation and/or xerostomia. As used herein, the term "treatment" refers to the treatment of dry mouth in a patient, such as a mammal (particularly a human), which includes alleviating one or more of the symptoms of dry mouth.

An effective, user-friendly and side-effect-free method to treat dry mouth would be highly desirable as those patients experience a significant compromised quality of life and oral health and available solutions to this condition are largely missing.

As can be seen, there is a need for a transcutaneous electrical stimulation device and method for applying a series of electrical pulses to the nerves that control salivary gland function. The present invention facilitates the increase of bilateral parotid glands salivation through transcutaneous electrical stimulation of the auriculo-temporal nerve. The person skilled in the art will be able to extend the use of the method of the present invention to other devices and uses, which would allow the use of electrical stimulation in other areas of the human body to improve the secreto-motor activity of similar surface glands (i.e., other salivary glands, lacrimal glands, etc.), or optimize the function of another internal secretory organs. In addition, this invention discloses a method to optimize the control and efficacy of electrostimulation of the salivary glands.

SUMMARY OF THE INVENTION

According to an aspect of the invention, a system to treat dry mouth is provided. The system is composed of a headset, the headset comprising an electronic control module, one or more elastic arms and one or more stimulating modules. The one or more stimulating modules are linked, each via an elastic arm, to the electronic control module. The electronic control module has a signal generator configured to generate electrical signals for stimulation, based on one or more values of one or more predefined or controlled parameters, a power supply, and control bottoms.

According to an additional feature of the invention, the system comprises, in addition to the headset, a mobile device that may be a remote control, a smartphone, a tablet or alike, and to which the electronic control module is connected wirelessly. In this configuration, the system is controlled either by the electronic control module, or by the mobile device, or by both.

According to another aspect of the invention, the electronic control module and/or the mobile device allow the users to control the stimulating module, i.e., timing of operation, and stimulation parameters (intensity, current, voltage, stimulation pattern, timing, type of stimulation, and the like).

According to another aspect of the invention, the headset is adaptable to engage the preauricular area, while being removably mounted one or more times on and from the user's head.

According a to another feature of this invention, the elastic arms are composed of a hollow mechanical housing carrying electric wires on the lateral cranial surface from the pre-auricular zone to the electronic control module.

According to still another feature of this invention, the headset is comprised, unilaterally or bilaterally, of a stimulating module, which incorporates a plate with a set of two or more electrodes contacting the user's skin at a neuro-sensitive areas (mainly the auriculotemporal nerves at the pre-auricular area), an ear-plug serving as anchoring pivot inserted in the ear canal, and an adjustment mechanism to selectively position the plate on a neuro-sensitive area.

According to still another aspect of the invention there is provided an adjustment mechanism that allows adjustment of the location of the plate with the electrodes in order to optimize the delivery of electrical stimulation to relevant neuro-sensitive areas. The adjustment mechanism is composed of the elastic arm bar and an elastic bar (part of the stimulating module), whereas both are connected to the ear-plug that serves as anchoring element. The elastic bar has a spring-like feature that approaches the plate to the skin of the user.

According to still another feature of the invention, the elastic bar can be rotated around the ear-plug, that serves also serves as axis. Moreover, the plate is attached to the elastic bar and may be moved along the elastic bar to be positioned in the most optimal position.

According to still another feature of the invention, the elastic bar may be sliced through the ear-plug in order to position the plate that is attached to it, in the most optimal position.

According to yet another feature of this invention, a plurality of electrodes that are part of the stimulating modules, are placed in the pre-auricular zone, wherein the electrodes are configured to apply electric signals for stimulating mainly the auriculotemporal nerve in the pre-auricular region to induce salivation and in addition stimulating the minor salivary glands inside the oral cavity.

According to still a further feature of the invention the electronic control module includes a power source such as a battery (either rechargeable—like Li-Ion, Li-Pol, or primary).

According to still another feature of the invention the signal generation has a microprocessor/ASIC, wireless transceiver modules, power source, DC to DC converters, sensors.

According to a more specific feature of this invention, the programmable microprocessor has the following functions: (a) communication with the wireless transmission module, (b) the general configuration of the input and output ports of the circuit, (c) the digital control of the voltage switching frequency by sending signals to an integrated voltage switching circuit, (d) the control of the voltage amplitude that the device can deliver by modifying the reference value, (e) processing information received from peripherals (i.e., pushbuttons of a remote control or smartphone application) in order to configure the operation modes, and (f) store the most updated configuration parameters in a non-volatile memory.

According to another specific feature of this invention, the communication module is a wireless module (transmitter and receiver) with an antenna, and is connected to the microprocessor. A firmware manages the communication with the wireless device. This firmware supports at different times the same configuration: constant burst and modulated mode. Characters '+' and '−' increase or decrease the signal strength respectively to a comfortable configuration for each person.

According to an additional specific feature of this invention, the electrostimulation is controlled through several modules: (a) An embedded module with a main code and libraries that can control peripherals of the microprocessor. (b) A main module that allows to initialize the peripherals through the libraries to process information and to execute the flow diagram. (c) A module that manages the communication implemented to control the wireless transceiver to send and receive data from the mobile device through a wireless or wired communication. (d) A module that controls the peripheral for signal generation used to control the voltage switching circuit. (e) A module that controls the communication used to send the data to the wireless transceiver or wired communication. (f) A module that controls the communication used to control the behavior of the sensing feedback circuit.

According to still another aspect of the invention, the system has a mobile device containing a wireless transceiver allowing the user to send commands to the stimulating module to change the configuration parameters.

According to a more specific feature of this invention, the mobile device may be a remote-control unit with pushbuttons that controls the configuration parameters sent to the stimulating device, a smartphone with an application that controls the configuration parameters sent to the stimulating device, or other mobile devices such as a tablet.

According to yet an additional characteristic of this invention, the smartphone can be used for any electrostimulation-based treatment of dry mouth, including the use of transcutaneous or percutaneous electrodes for nerve and/or muscle activation generating stimulation of any component of the salivary reflex arch, such as the salivary glands and their nerves or acupuncture points associated to salivary gland function, which activates the salivary glands for the increased production of saliva.

According to still further features of the invention, the electronic control module includes a switch to turn on and off the device, and to increase or decrease stimulus intensity by changing parameters such as amperage, voltage, frequency and duty cycle.

According to still further features of the invention, the materials of the devices comprise vinyl, silicone, acrylate, ceramic, polymers, metal, metal alloys or other dental material, or any combination thereof.

According to still further of the invention, the material of electrodes may be bio-compatible.

According to still further features of the invention, the electrodes surface may be finished with electropolish, coated with polymers, plated with gold, platinum-iridium alloy silver, nickel, platinum, silver, silver-oxide, copper, titanium oxide or any combination thereof.

According to still further features in the described embodiments, the signal generator includes a mechanism for producing a series of pulses having amplitude of about half to ten volts, a pulse width of about 50 microseconds to 5 mSec, 250 microseconds or 1 millisecond; and a frequency between 0.1 Hz and 200 Hz. Further, the impulses may be uni-polar or bi-polar pulses.

According to still further features in the described embodiments, the electronic control module is provided with a display to present the stimulation level in both numeric and alpha-numeric characters.

According to still further features in the described embodiments, the distance between the electrodes may range from 1 millimeter to 150 millimeters.

These and other features, aspects and advantages of the present invention will become better understood with reference to the following drawings, description and claims.

BRIEF DESCRIPTION OF THE DRAWINGS

FIG. 29 shows the changes in the VAS values of the experiment;

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Referring to FIGS. 1 through 6, the present invention may include a system designed to increase salivary flow for people suffering from dry mouth, through extra-oral transcutaneous electrostimulation. One embodiment embodies a headset with the following main parts: (I) one or more stimulating modules, (II) one or more elastic arms (each for each stimulating module), and (III) an electronic control module. The stimulating module is composed by the following main parts: (a) a plate containing the stimulating electrodes, that is attached to the user's skin, (b) an ear-plug to be inserted in the ear canal, serving as anchoring element for the headset and as axis that allows the plate to rotate around the ear-plug; and (c) an adjustment element composed of an elastic bar that holds the plate, approaches it to the user's skin by a spring-like mechanism and in addition allows the plate to slide forward and backward. The elastic arm(s) and the elastic bar(s) provide an adjustment mechanism that enables the positioning of the electrodes in the most favorable neuro-sensitive area. However, it should be noted that the system may also have other configurations.

For using the system, the headset is placed on the head of the user (the arch can be placed on top of the head, like in standard earphones, or at the back of the head), while the stimulation module covers the neuro-sensitive areas that are known to be associated with the salivary gland function such as the auriculotemporal nerve, the salivary glands or the acupuncture points. The region of the skin can (optionally) be previously wetted with a conductive gel.

The system is controlled either by built-in (into the electronic control module) control buttons or by a mobile device such as a remote control (custom or Commercial Off The Shelf), a smartphone, a tablet, a laptop—to which the electronic control module is wirelessly communicated (by technologies as Bluetooth, ZigBee, NFC, and the like). The electronic control module and the mobile device incorporate an application allowing setting of the preferred parameters: timing of operation, stimulation parameters (intensity, current, voltage, stimulation pattern, and the like and any combination thereof), aimed at optimizing the stimulation and ease of use. Upon switching the system on, the behavior of the system can be changed with the electronic control module, or via the mobile device application.

Figure 30:
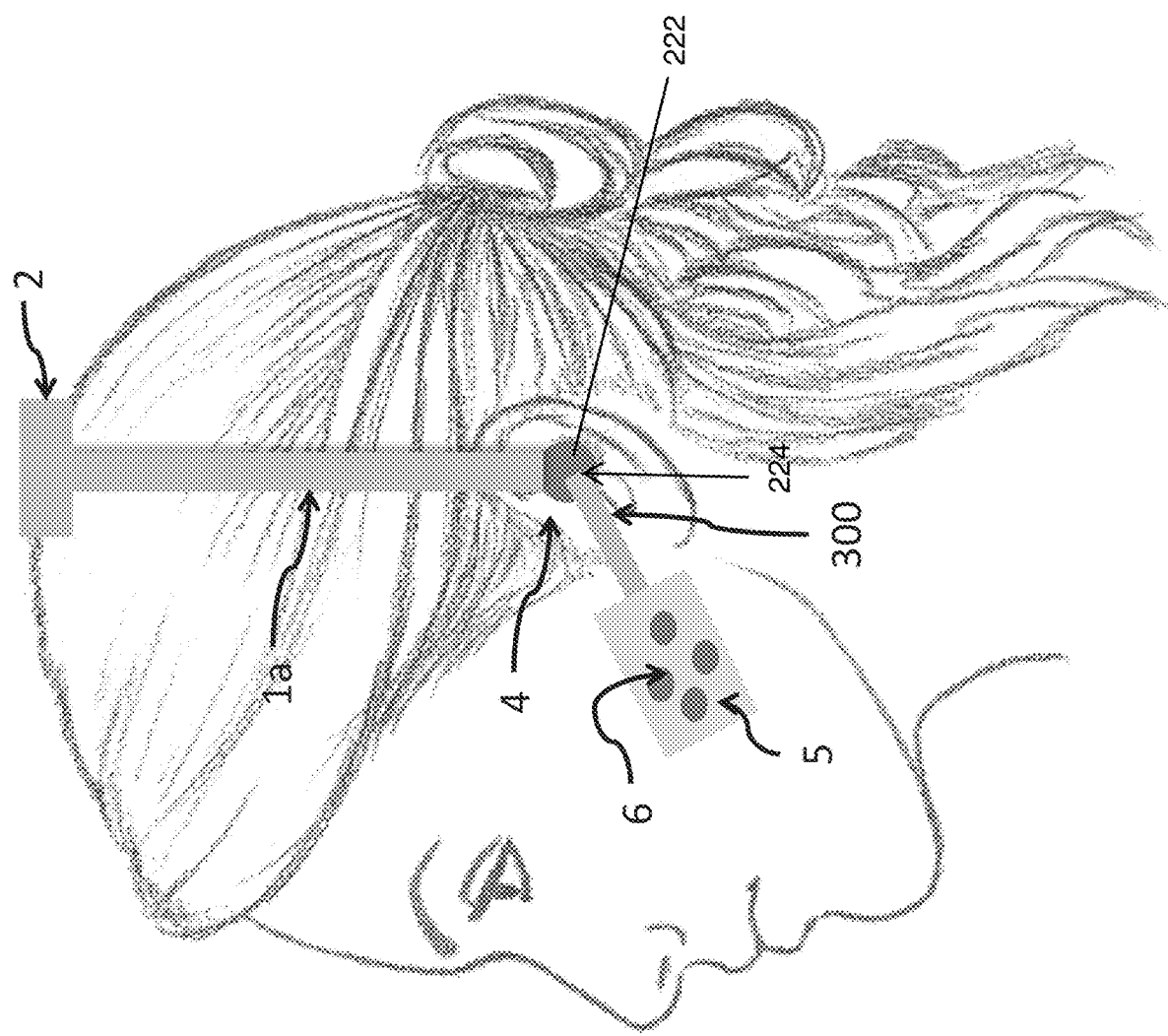
FIG. 30 depicts a side-view of a user wearing the headset and in particular the stimulating module.

(I) One or more stimulating modules: The stimulating module may be adapted to be operatively associated with the preauricular/parotid area (a neuro-sensitive area as it covers the auriculo-temporal nerves that innervate the parotid gland), or with an acupuncture area, leading to increased salivary secretion. The stimulating module may be comprised of the following components:
 a. A plate that contains the stimulating electrodes aimed at delivering the electrical stimulation to the neuro-sensitive area. The plate may be selectively held by an elastic bar.
 b. An anchoring element adapted to be selectively inserted in the ear canals, a deterministic and fixed location in each individual, and helps stabilizing the system in its place. The ear-plug has, in one embodiment, a shape and material similar to a standard acoustic earphone. The ear-plug is connected to the elastic arm and comprised of two main elements: the plug itself that is inserted in the ear canals and a pivot 222 to hold the elastic bar and allowing it to rotate around the ear-plug. In an additional configuration the pivot may have a canal/groove 224 to allow the elastic bar to slide forward and backward, as illustrated in FIG. 30.
 c. An adjusting element that is either an elastic bar or a flexible joint such as ball and socket joints, swivel joint, and the like, or a combination thereof, that connects between the ear-plug and the plate. The elastic bar attaches the plate to the skin by a spring-like mechanism and allows sliding of the plate forward and backward.

(II) One or more elastic arms: Each stimulating module is joined to the electronic control module by elastic arms of the headset that extend through the lateral cranial surface and contain wires for electrical connection between the electronic control module and the stimulating module.

(III) Electronic control module: Bound to the elastic arms in one embodiment, the electronic control module is comprised of the following components:
 a. A printed circuit board (PCB), which has layers of conductors with tracks, a distribution that allows connecting electronic components such as microprocessors, transceiver modules, power source, among others.
 b. A DC to DC converter circuit responsible for increasing or decreasing the voltage of the power source using a voltage reference obtained from a sensing feedback circuit or a similar circuit. It is also used to obtain high voltage on the electrodes and a voltage switching to get the desired waveform.
 c. A microprocessor, whose functions are (1) communication with the wireless transmission module, (2) the general configuration of the input and output ports of the circuit, (3) the digital control of the voltage switching frequency by sending signals to an integrated voltage switching circuit, (4) the control of the voltage amplitude that the system can deliver by modifying the reference value, (5) processing information received from peripherals (i.e., pushbuttons of a remote control or smartphone application) in order to configure the operation modes, and (6) store the most updated configuration parameters in a non-volatile memory.
 d. A wireless module (transmitter and receiver) with an antenna coupled to the main PCB and connected to the microprocessor. A firmware manages the communication with the wireless device.
 The firmware controls other functions of the system, including the control on an increase or a decrease level of the stimulation signal strength respectively to a comfortable configuration for each person.
 e. Passive components including, but not limited to, capacitors, resistors, transformers and diodes located in the PCB of the system, which are:
  1) Indicators of the state of charge of the battery, power on and data.
  2) A power on/off switch.
  3) Capacitors, resistors and diodes.
  4) A device for increasing the output voltage.
 f. A connector for using an external power source to feed the voltage of the system or to recharge the internal battery.
 g. A power source like a primary cell or rechargeable battery like Ni—Cd, Li-Ion, Li-Pol. and a system to recharge it coupled to the casing and electrically attached to the main PCB as the main power source element of the stimulating module.

(IV) Mobile device: The mobile device may include the following components that are related to the system:

a. A device with wireless communication module or wired sockets for connecting to the stimulating module to the electronic control module.
b. The wireless communication system may consist of a bi-directional communication, two or more antennas, connecting to/from mobile device for the transmission of configuration parameters.
c. The wired communication system, in another embodiment, can be USB, Micro USB, I²C and the like which is used for the transmission of configuration parameters to the stimulating module.
d. In another embodiment the electronic control module may be an application of a mobile smartphone device.

In summary, the electrostimulation is controlled through one of several devices and modules, or any combination thereof:
a. An embedded module with a main code and libraries that can control peripherals of the microprocessor.
b. A main module that allows to initialize the peripherals through the libraries to process information and to execute the flow diagram.
c. A module that manages the communication implemented to control the wireless transceiver to send and receive data from the mobile device through a wireless or wired communication.
d. A module that controls the peripheral for signal generation used to control the voltage switching circuit.
e. A module that controls the communication used to send the data to the wireless transceiver or wired communication.
f. A module that controls the communication used to control the behavior of the sensing feedback circuit.

In one embodiment, the system uses a mobile device with an application that controls the parameters of the stimulating module. This application is adapted to define the waveform, signal strength, voltage, current, pulse shape, frequency, start time, stop time, and any combination thereof. The firmware deciphers the command coming from the application at the mobile device and translates it into a specific stimulation pattern, using a special library to control the stimulation module. The following figures are given merely as examples of different embodiments and configurations of the present invention.

Figure 1:
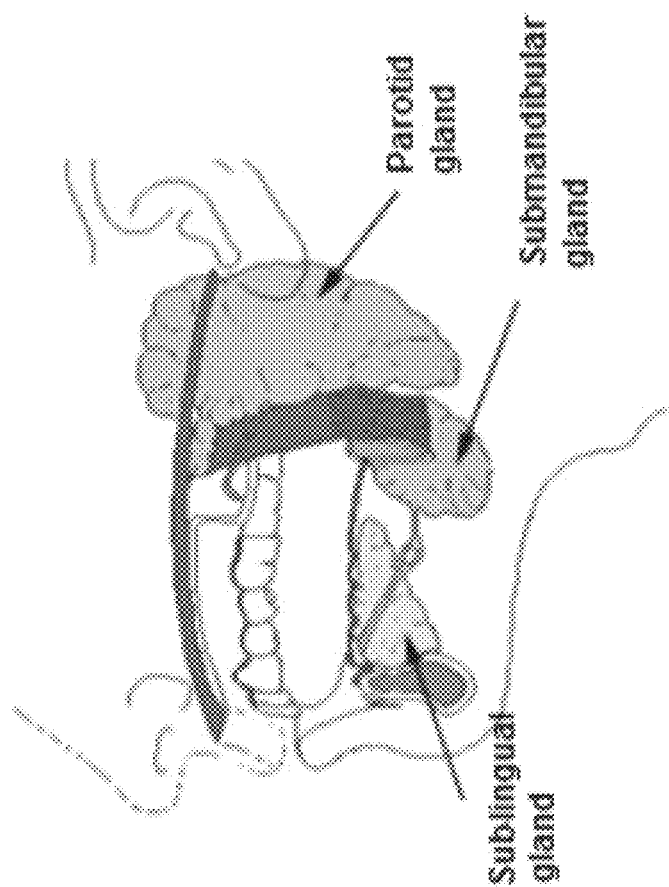
FIG. 1 is a schematic view of the major salivary glands in the oral cavity (minor salivary glands are not shown)

Referring to FIG. 1 a schematic view of the major salivary glands in the oral cavity (minor salivary glands are not shown). Stimulation of various kinds, such as mechanical (chewing a gum as an example), sensory such as smell of food, psychological such as anxiety, drugs such as pilocarpine, electrical stimulation such as TENS, and other factors are contributing to an increase (or decrease) of saliva secretion from the salivary glands.

Figure 2:
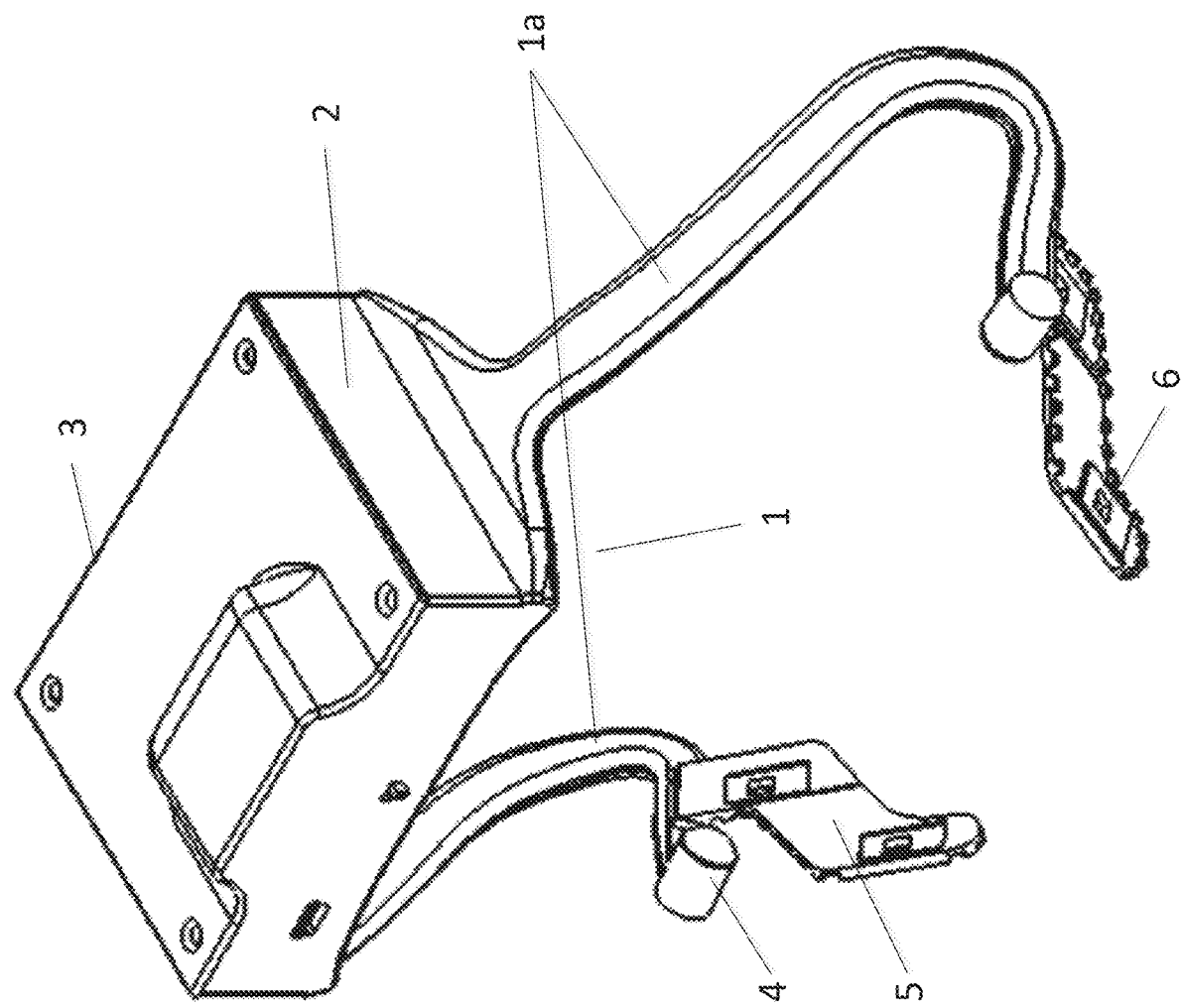
FIG. 2 shows an embodiment of the stimulating system of the present invention, which illustrates the outside of the headset.

FIG. 2 illustrates the headset according to the present invention. Here a mechanical, hollow and rigid mechanical housing 1 is observed. The housing 1 is comprised of a box 2 and its cover 3 containing the electronic control module. Elastic arms 1a emerge from the sides of this box, uni or bilaterally and postero-anteriorly, being fixed in a position and stabilized by an ear-plug 4 inserted into the external meatus of the ear for anchoring. Each elastic arm carries the wiring from the electronic control module to the plate 5 that is part of the stimulating module and holds electrodes 6 on the skin.

Figure 3:
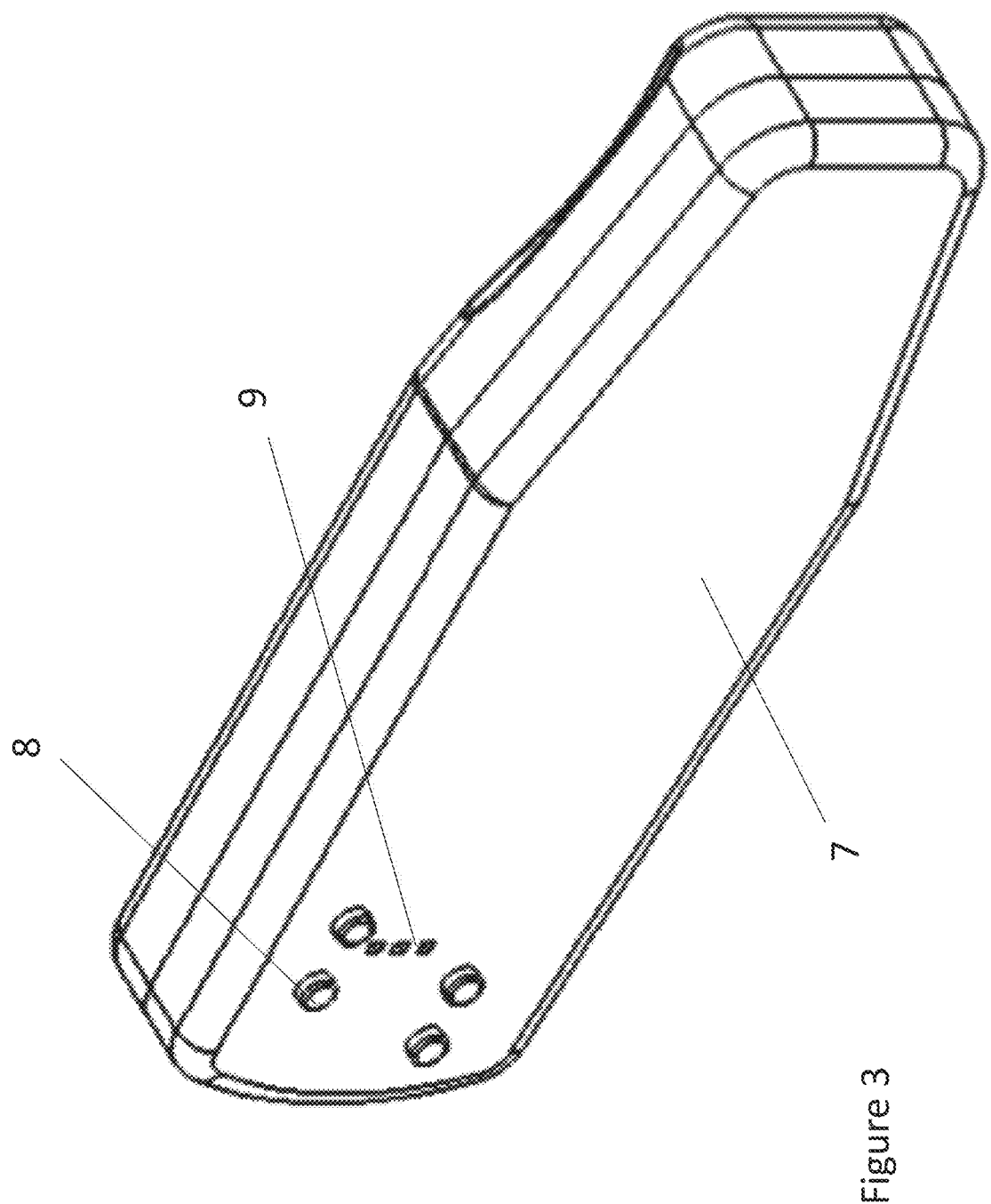
FIG. 3 shows an embodiment of the mobile device used in accordance with the method of the present invention.

FIG. 3 shows a mobile device according to the present invention. A mechanical, hollow, rigid polymer housing 7 is shown. Buttons 8 regulate the parameters of stimulation. Indicators 9 corresponding to modes of stimulation for operating the system are inserted near the control buttons.

Figure 4:
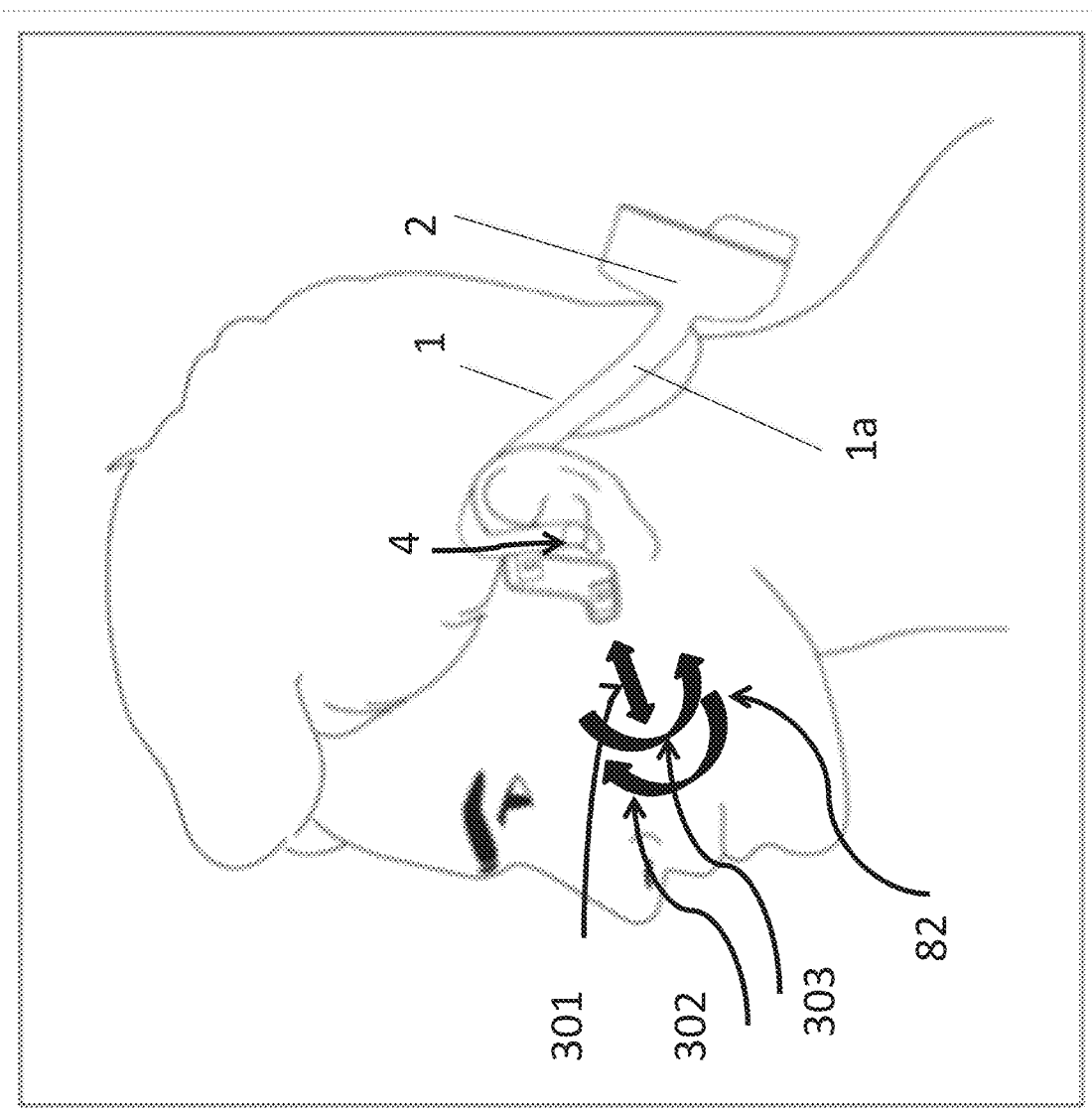
FIG. 4 shows an embodiment of the stimulating system of the present invention, which illustrates the headset fixed to the user's head; as shown the position of the stimulating module can be adjusted in a rotational axis and lateral axis using the ear canal as an anchor.

FIG. 4 shows the headset 1 as carried by a user 82, where in one embodiment, the box containing the electronic control module 2 is placed at the back of the head (in another optimal embodiment the elastic arms 1a and the electronic control module are on the top of the head). In addition, the optional adjustments of the stimulating module are shown, where the plate can be rotated around the pivot point in the ear-plug 4 clock-wise 302 and contra clock wise 303 and closer to or further from 301 the ear-plug 4.

Figure 5:
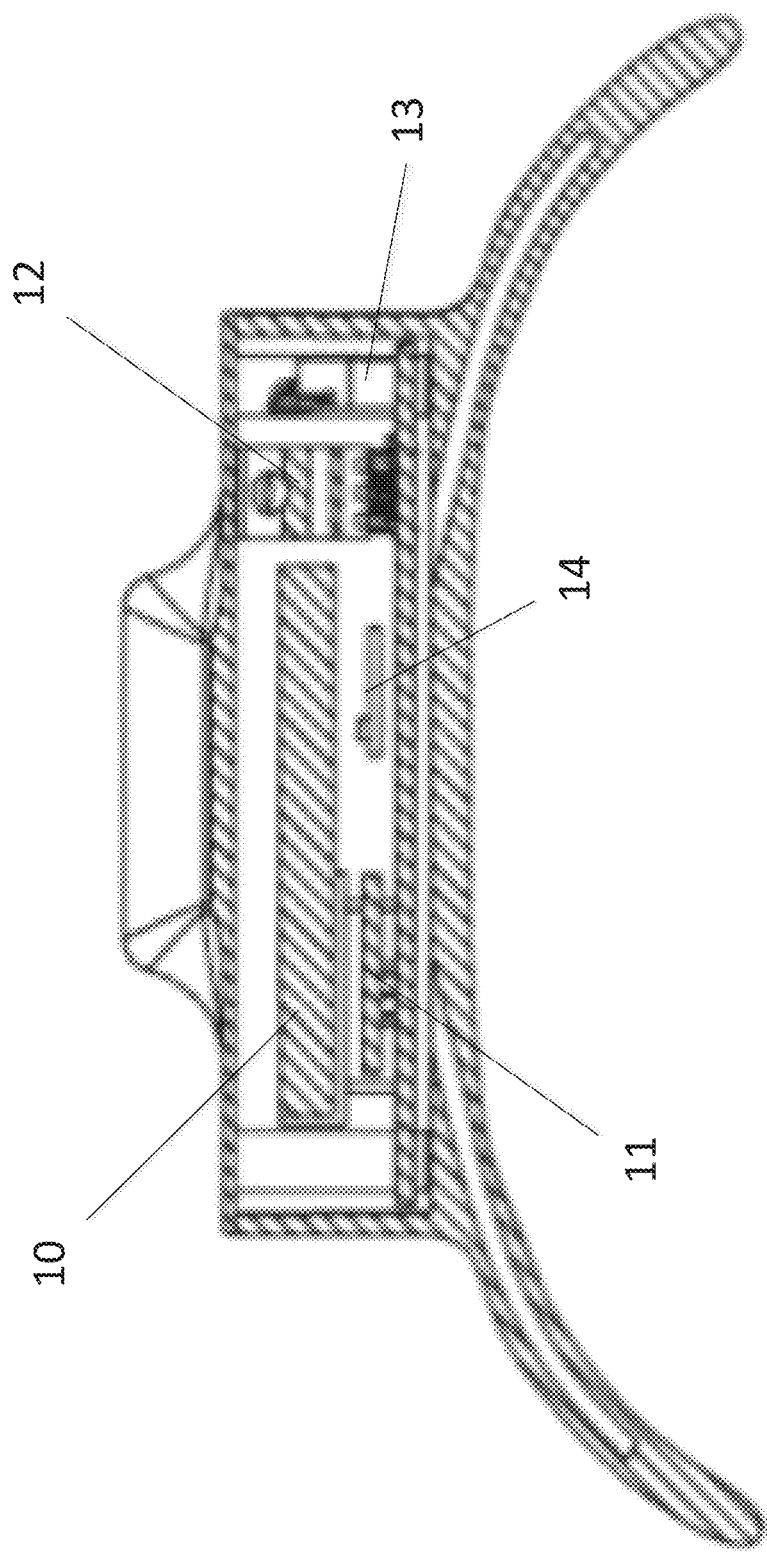
FIG. 5 illustrates a longitudinal section of the box of the electronic control module used in accordance with the method of the present invention.

FIG. 5 shows a longitudinal cross-section of the box containing the electronic control module. This figure depicts the battery 10, the micro-controller 11, transistors 12, the battery connector 13, and the DC-DC converter 14.

Figure 6:
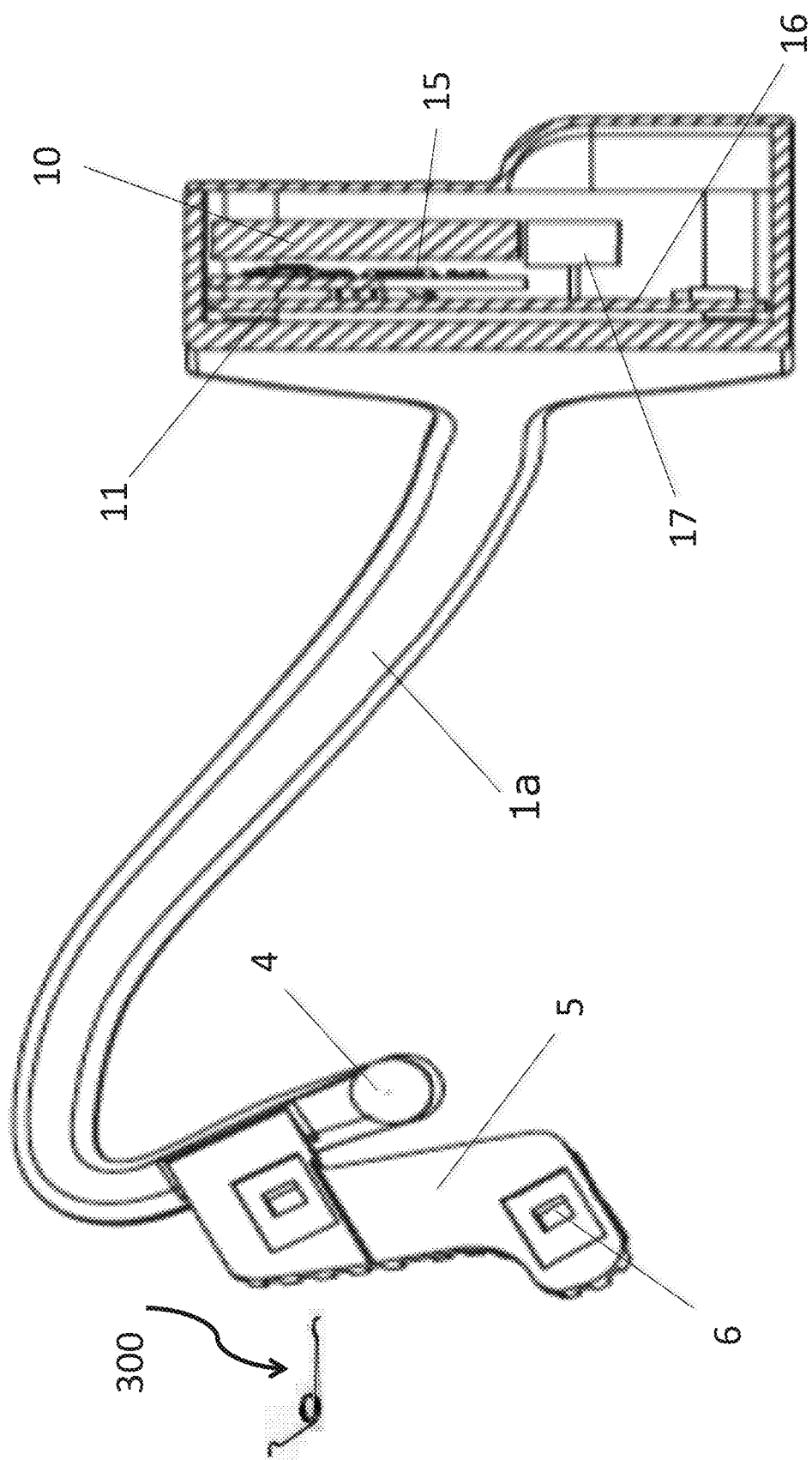
FIG. 6 illustrates a transversal section of the box containing the electronic control module linked to an elastic arm, used in accordance with the method of the present invention; the plate with the electrodes are pushed toward the skin of the cheek using a spring-like mechanism.

FIG. 6 shows a view of the headset with the elastic arm 1a, the ear-plug 4, the plate 5, the elastic bar 300 that due to its spring-like nature retains the position of the plate 5 toward the skin, and on the right side of the figure, a transversal cross-section of the box containing the electronic control module. This figure depicts the micro-controller 11, the battery 10, the wireless antenna 15, the PCB of the components 16 and the transformer 17.

Figure 7:
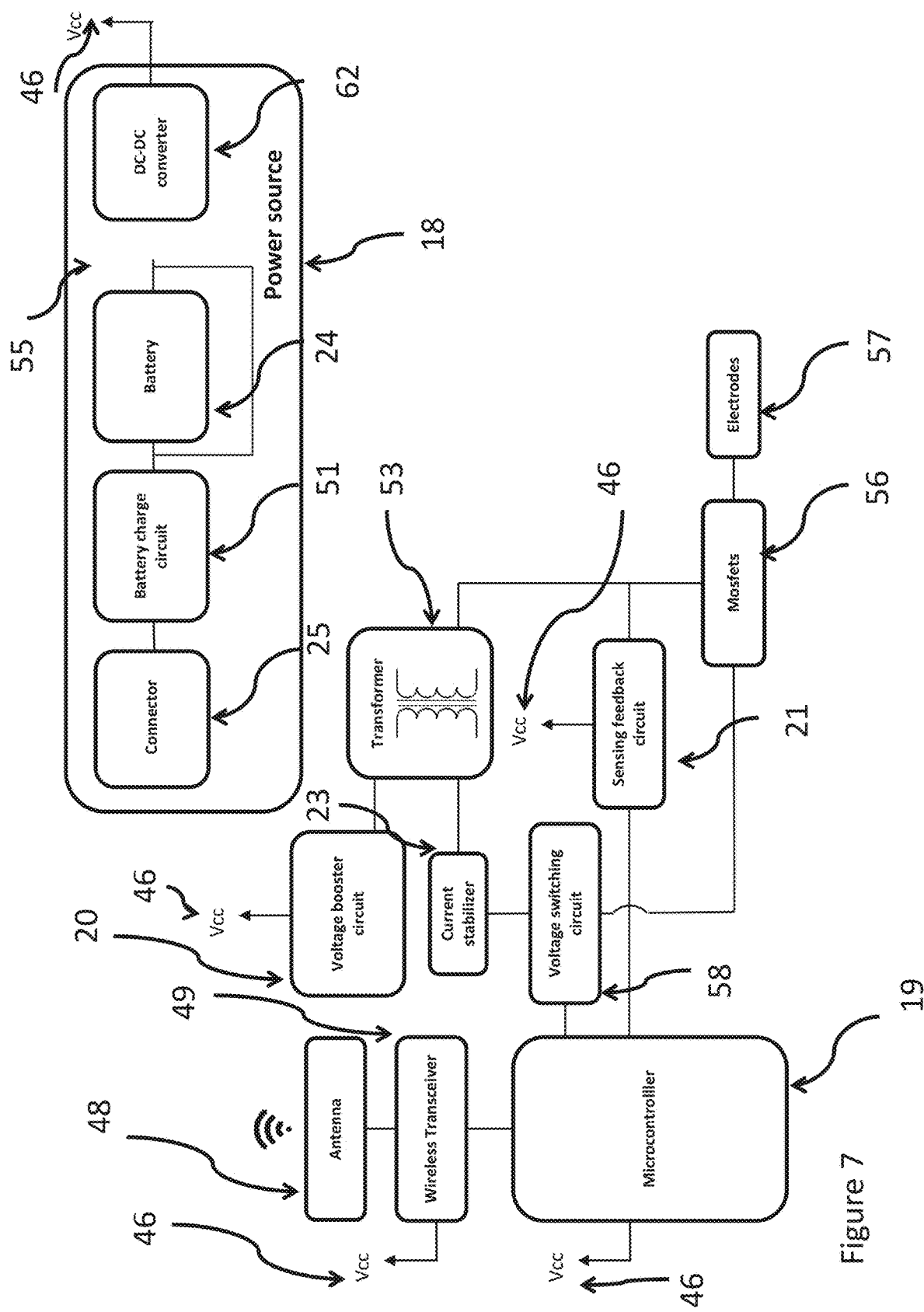
FIG. 7 shows a block diagram of the interconnection of the electronic control module of the stimulating system used in accordance with the method of the present invention.

FIG. 7 shows a general block diagram of the electronic control module depicting the power source 18 of the system that has a connector 25, a battery charge circuit 51, a battery 24, a switch 55, a DC-DC converter 62, and a voltage supply (Vcc) 46. The figures also display a microcontroller 19 working as the main control of the device, connected to a wireless transceiver 49, with an antenna 48, simultaneously connected to a voltage switching circuit 58, and a sensing feedback circuit 21. All the above connections are linked to several circuits such as a current stabilizer 23, a transformer 53, a voltage booster circuit 20, transistors 56, and electrodes 57.

Figure 8:
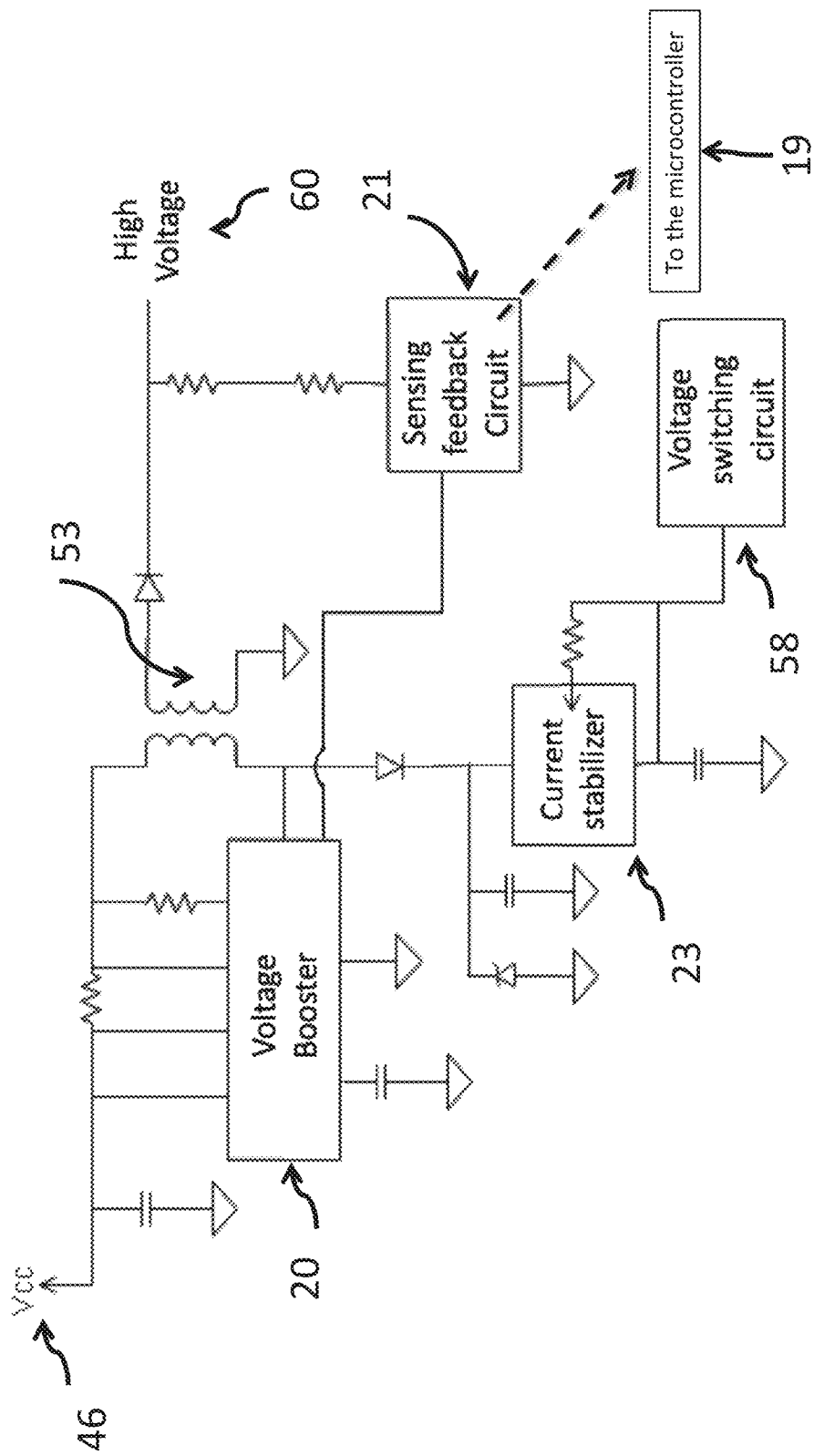
FIG. 8 illustrates an electronic schematic of the voltage booster circuit and the sensing feedback circuit of the stimulating system in accordance with the method of the present invention.
Figure 9:
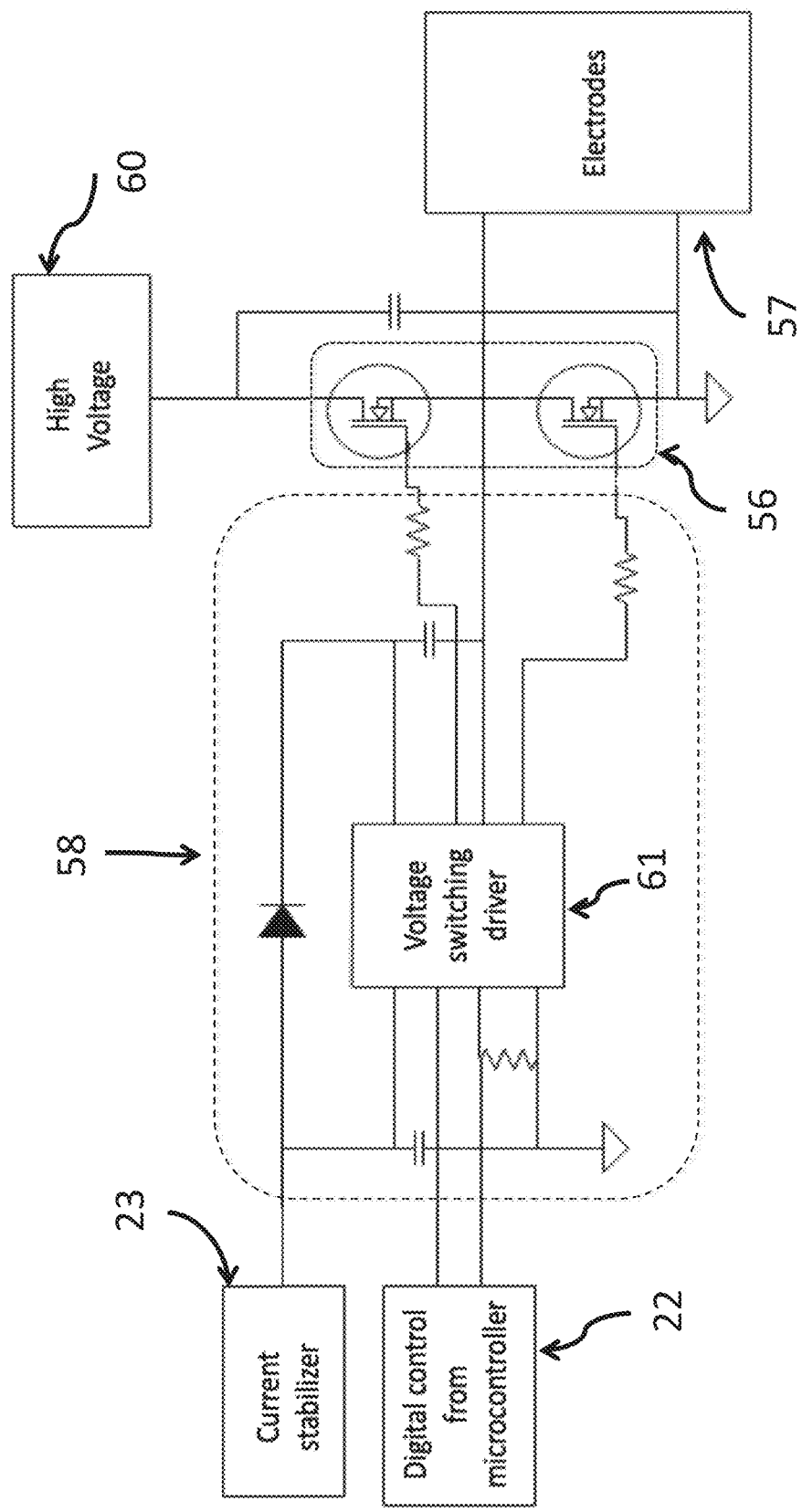
FIG. 9 illustrates an electronic schematic of the voltage switching circuit of the stimulating system used in accordance with the method of the present invention.
Figure 10:
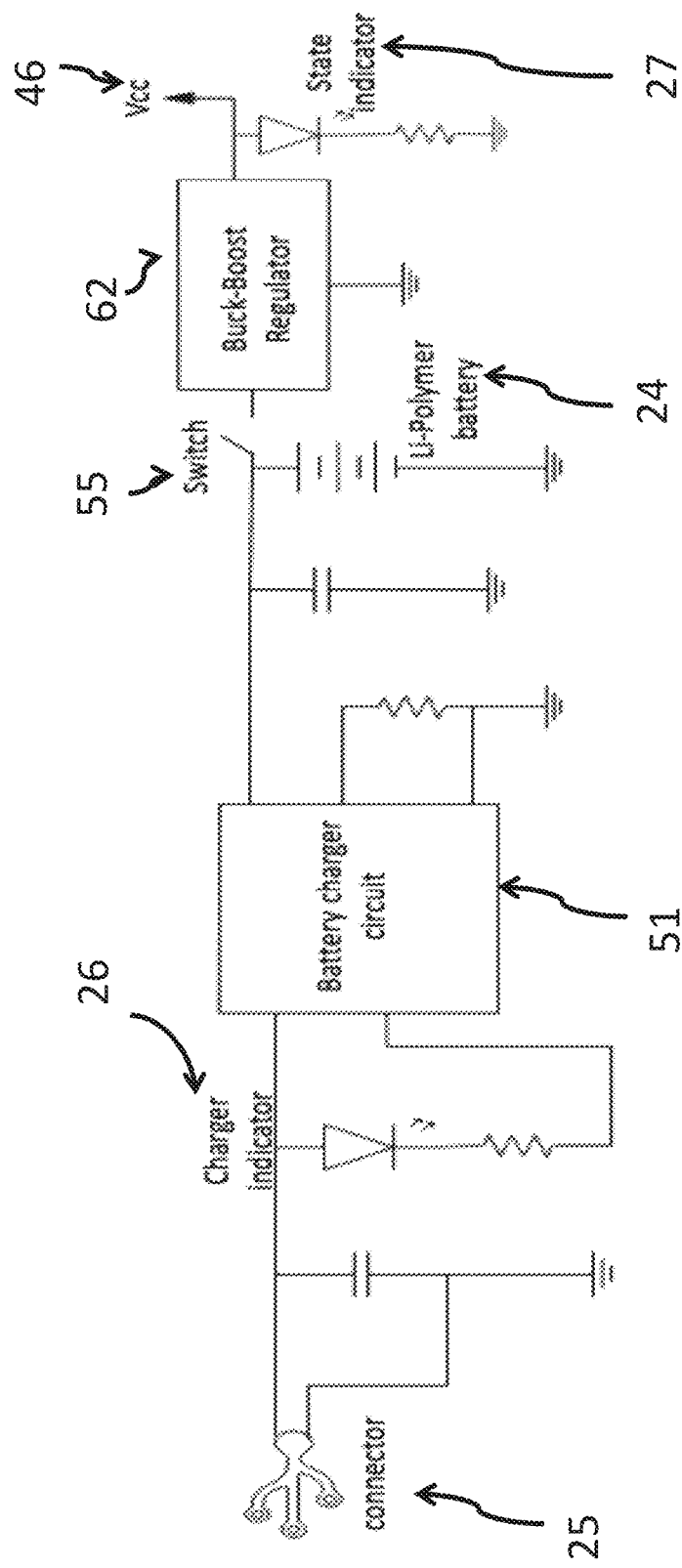
FIG. 10 illustrates an electronic circuit diagram of the battery charging circuit and the main power source of the stimulating system used in accordance with the method of the present invention.

FIGS. 8 to 10 illustrate electronic schematics of the interconnections employed inside the system of the current invention. FIG. 8 depicts the voltage booster circuit 20 and a transformer 53 to obtain high voltage 60 on the output. It also shows a diagram of a sensing feedback circuit 21 whose output is used as a reference and is also sent to the microcontroller 19 to measure and control the current voltage. Other depicted elements are a current stabilizer 23, and a voltage switching circuit 58.

On the other hand, FIG. 9 illustrates the electronic diagram of the voltage switching circuit 58 using two transistors 56 connected to a voltage switching driver 61, being digitally controlled by a microcontroller 22 and sourced by a current stabilizer 23.

FIG. 10 shows the electronic diagram of the battery charging circuit 51 that allows that a connector 25 works as a source of voltage; it also has a charger indicator 26 and a state indicator 27. An on/off switch 55 controls the start of the system. A buck-boost regulator 62 assures an appropriate voltage supply (Vcc) 46. A person skilled in the art understands this configuration and possible variants that it may have.

Figure 11:
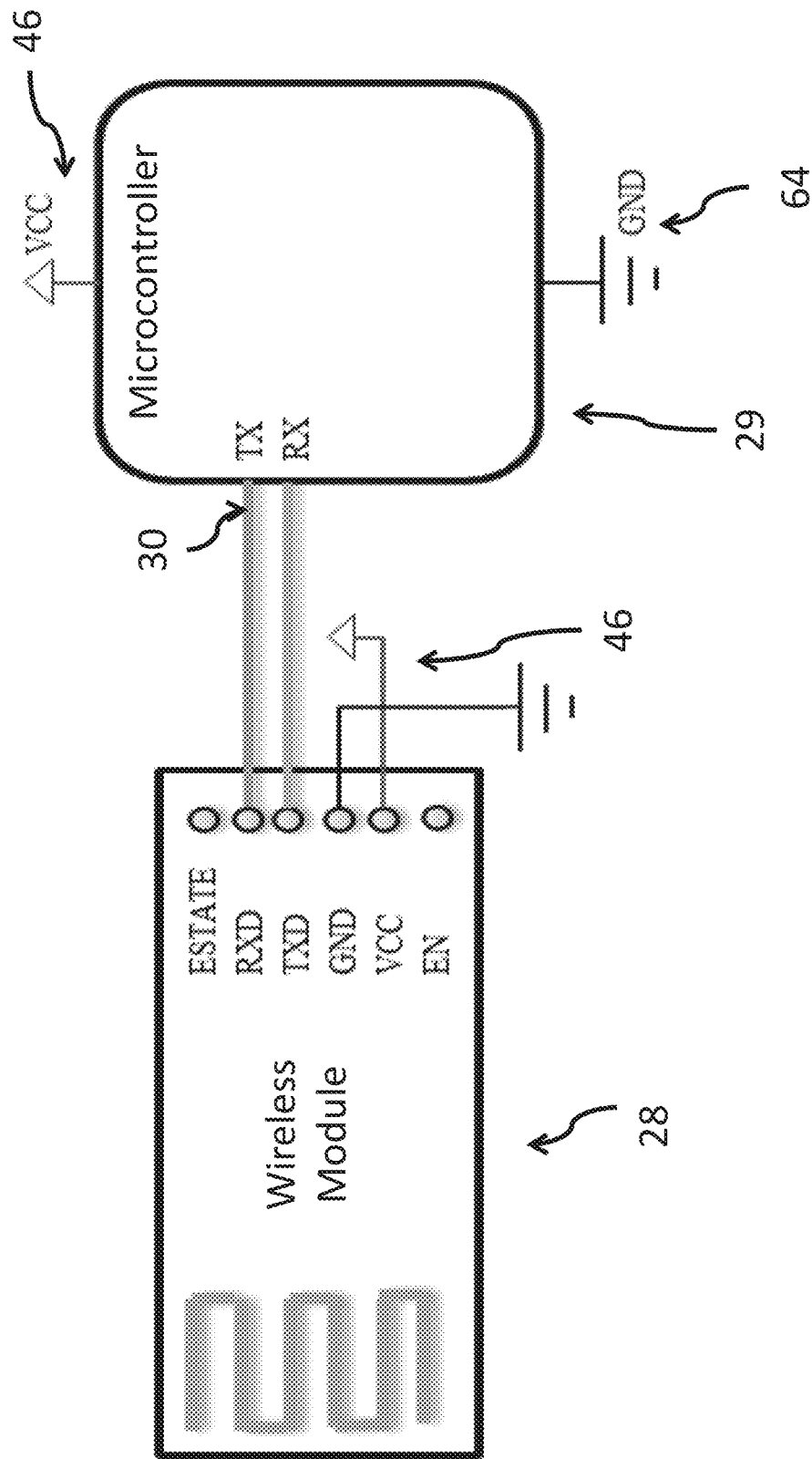
FIG. 11 illustrates the wireless module of the electronic control module and the microprocessor of the stimulating system used in accordance with the method of the present invention.

FIG. 11 shows the wireless module of the electronic control module 28 and the micro-controller 29 that are both connected through two pins 30, where data is sending. All the anterior devices are connected to the Vcc 46 and to ground (GND) 64.

Figure 12:
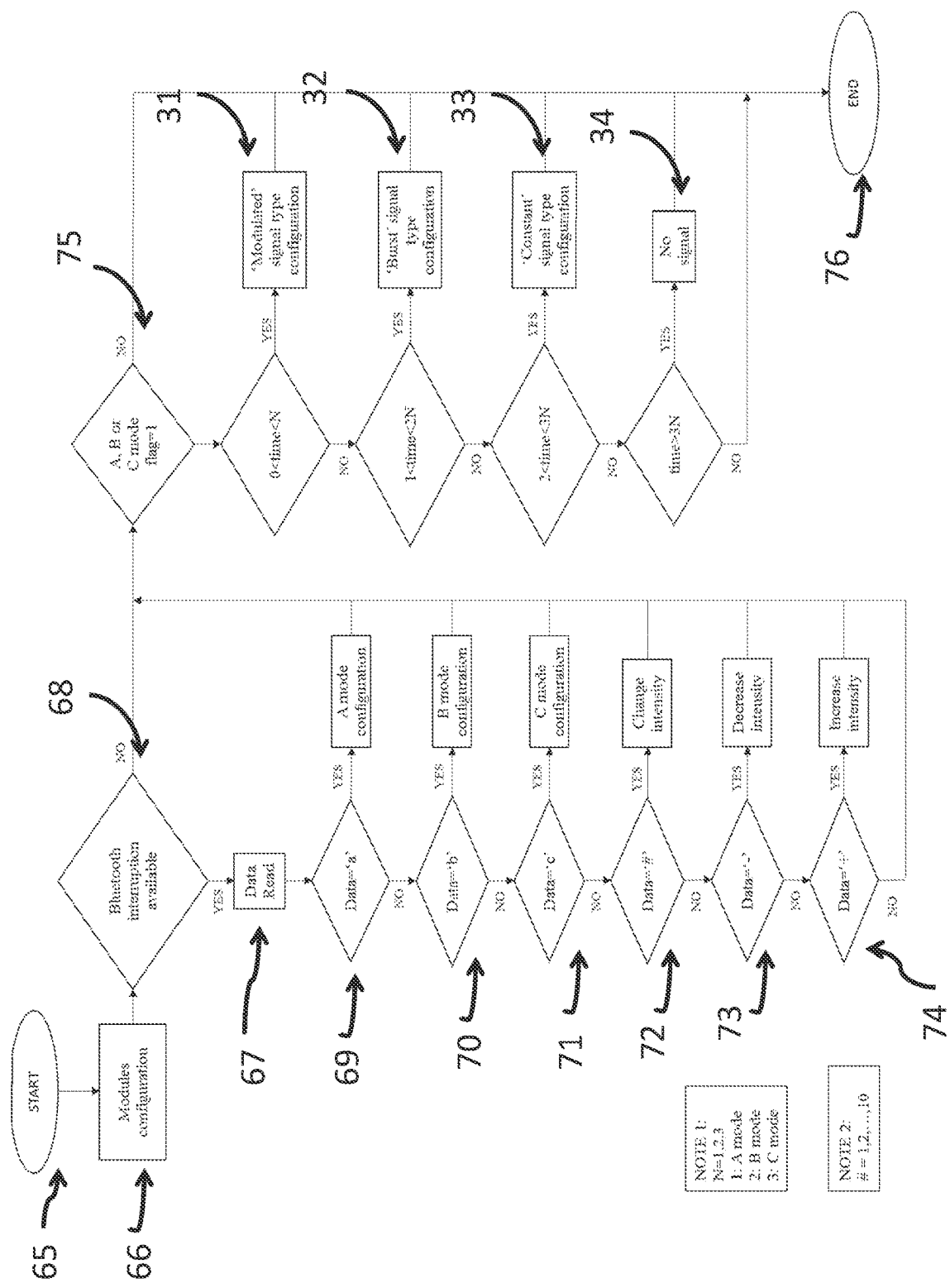
FIG. 12 illustrates the main flowchart of the system, that represents the global modules of the system.

FIG. 12 shows the flowchart of the system. At the beginning there is a start signal 65 in order to perform the modules configurations 66. Afterwards the system is waiting for special interruption 68, and when the interruption is available the data is read 67. There are six possible data: "a" 69 to activate the A mode configuration, "b" 70 to activate the B mode configuration, "c" 71 to activate the C mode configuration, "#" 72 to change intensity, "−" 73 to decrease intensity, "+" 74 to increase intensity. Then, a flag mode turns high 75 to generate three signals types progressively: the first one is a modulated signal 31, followed by a burst signal 32 and the last one a constant signal 33. Afterwards the signal is turned off 34; and the flowchart ends 76. The user can start 65 the process again sending a special character.

Figure 13:
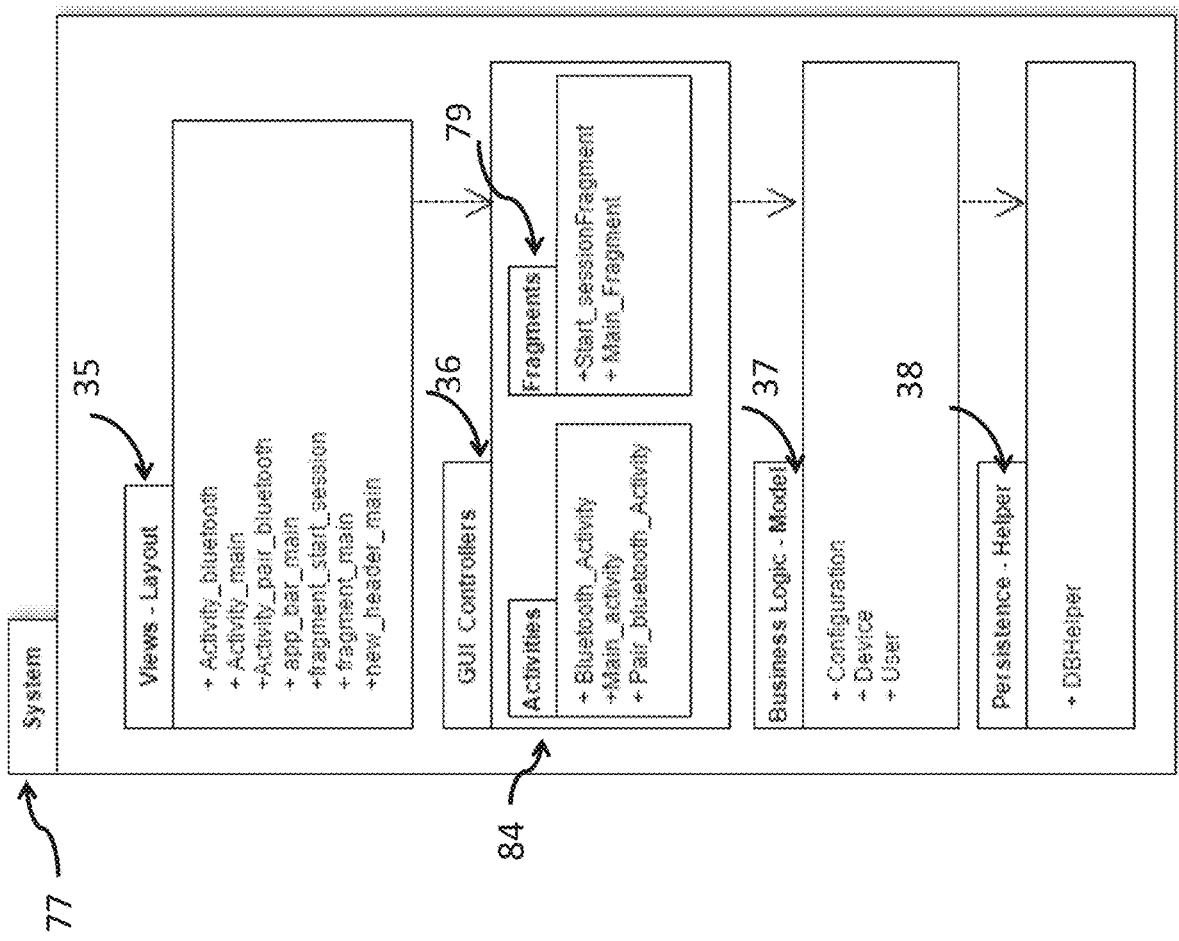
FIG. 13 illustrates the logic model to control the system and a package diagram.

FIG. 13 shows logic-model 37 to control the system through the mobile device. The application of the mobile device is composed mainly by the following packages: (i) View-Layout 35: Handles the GUI (Graphical User Interface) through the activities; (ii) Controllers 36: Perform all the logic and event management of the activities 84 and fragments 79 for all views; (iii) Logic-Model 37: Contains the main logic of the application, processing and sending signals to the electronic control module inside the headset and user's login; (iv) Persistence-Helper 38: Contains the main class that will allow transactions to the Database.

Figure 14:
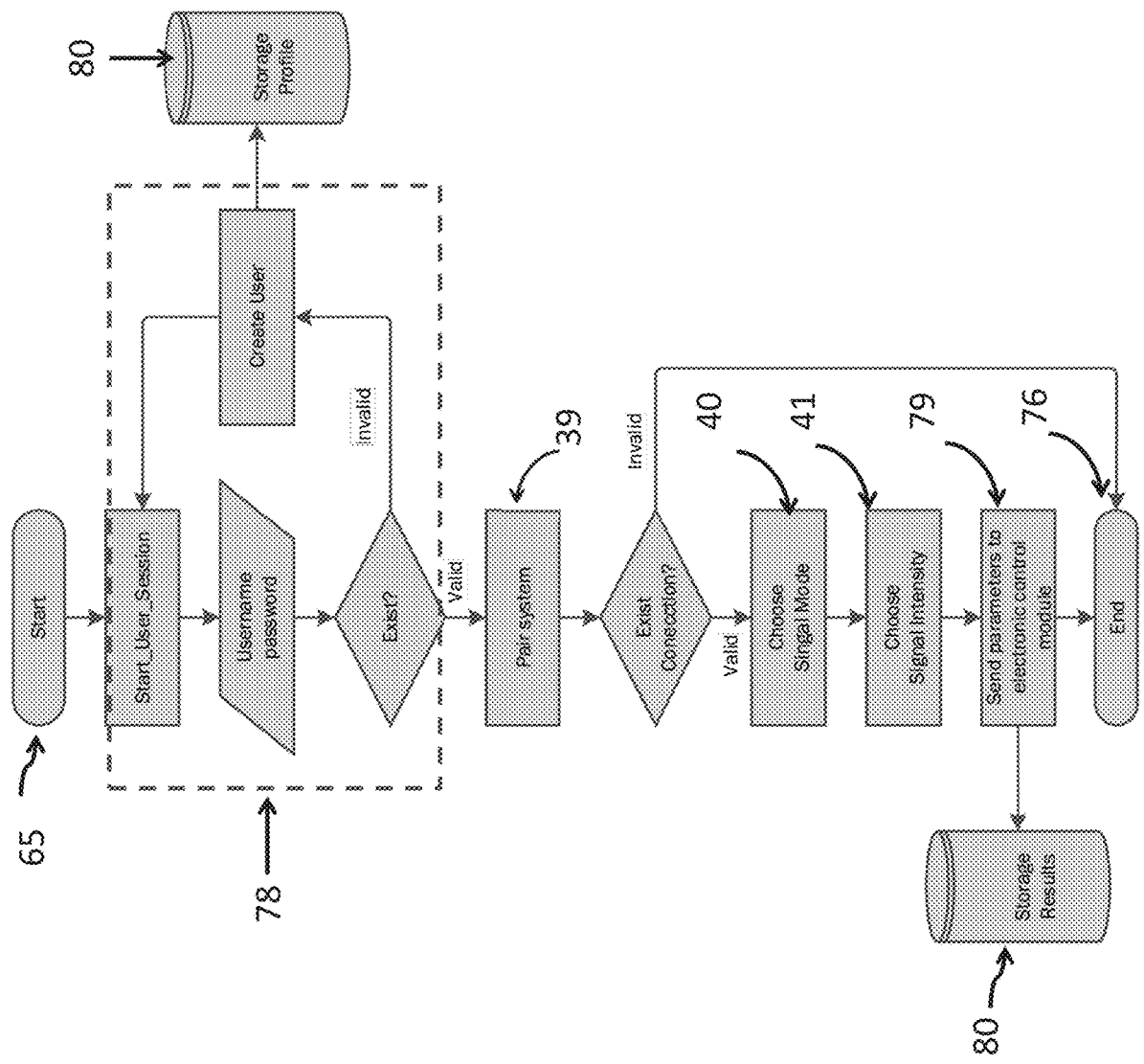
FIG. 14 illustrates the main flowchart of the mobile device application.

FIG. 14 shows the main flowchart of the mobile application. The application starts 65 with the creation of the new profile user 78. Afterwards, the mobile device is paired 39 with the system. Then the user can choose the signal mode 40 and the signal intensity 41; these are sent to the electronic control module inside the headset 79. The data is stored inside database 80, and then, the process ends 76.

Figure 15:
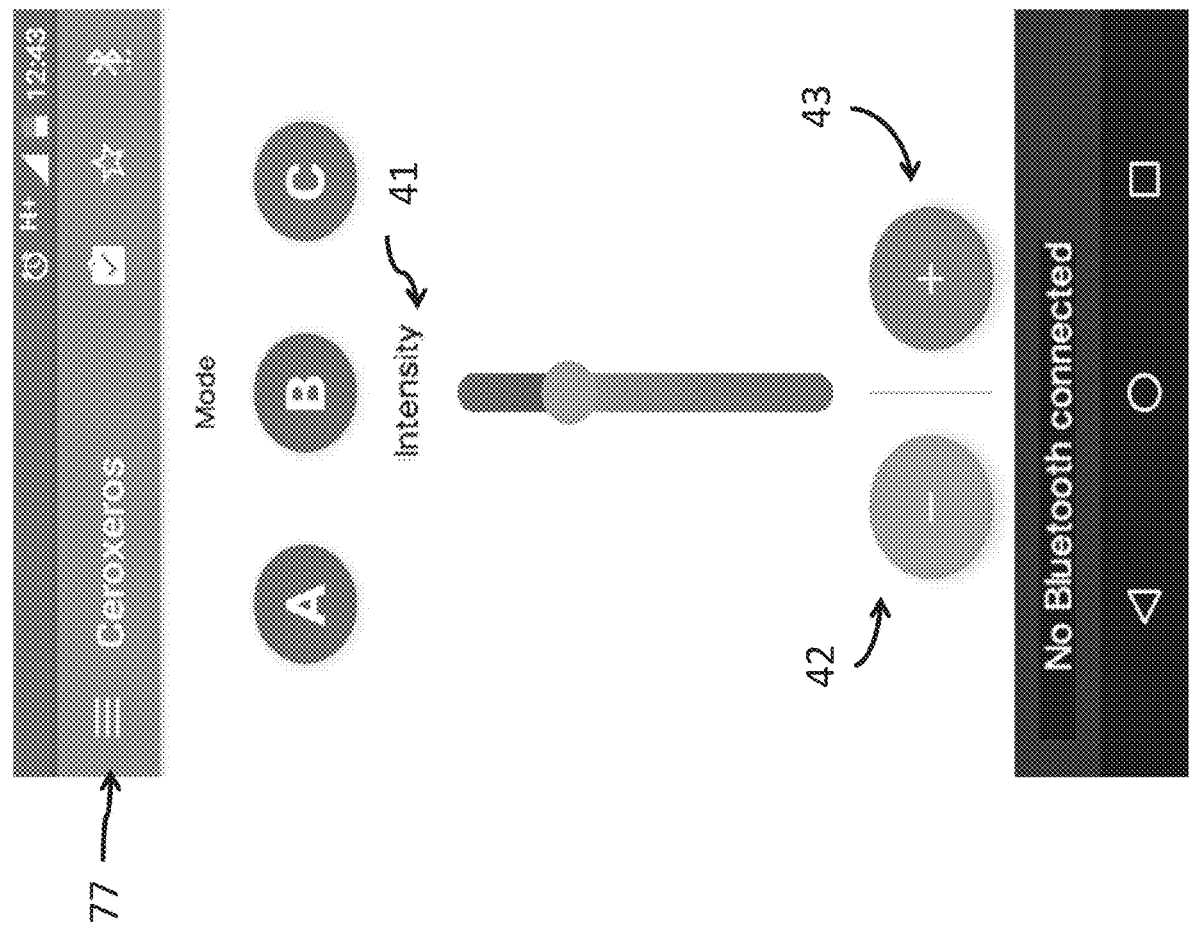
FIG. 15 illustrates an image of the screen capture of the mobile device application.

FIG. 15 shows a screen image of the application of a mobile device adapted to modulate intensity 41 through the serial module receiving a byte character: '−' 42 to decrease the intensity, or '+' 43 to increase it. The menu of the app is accessed directly 77.

Figure 16:
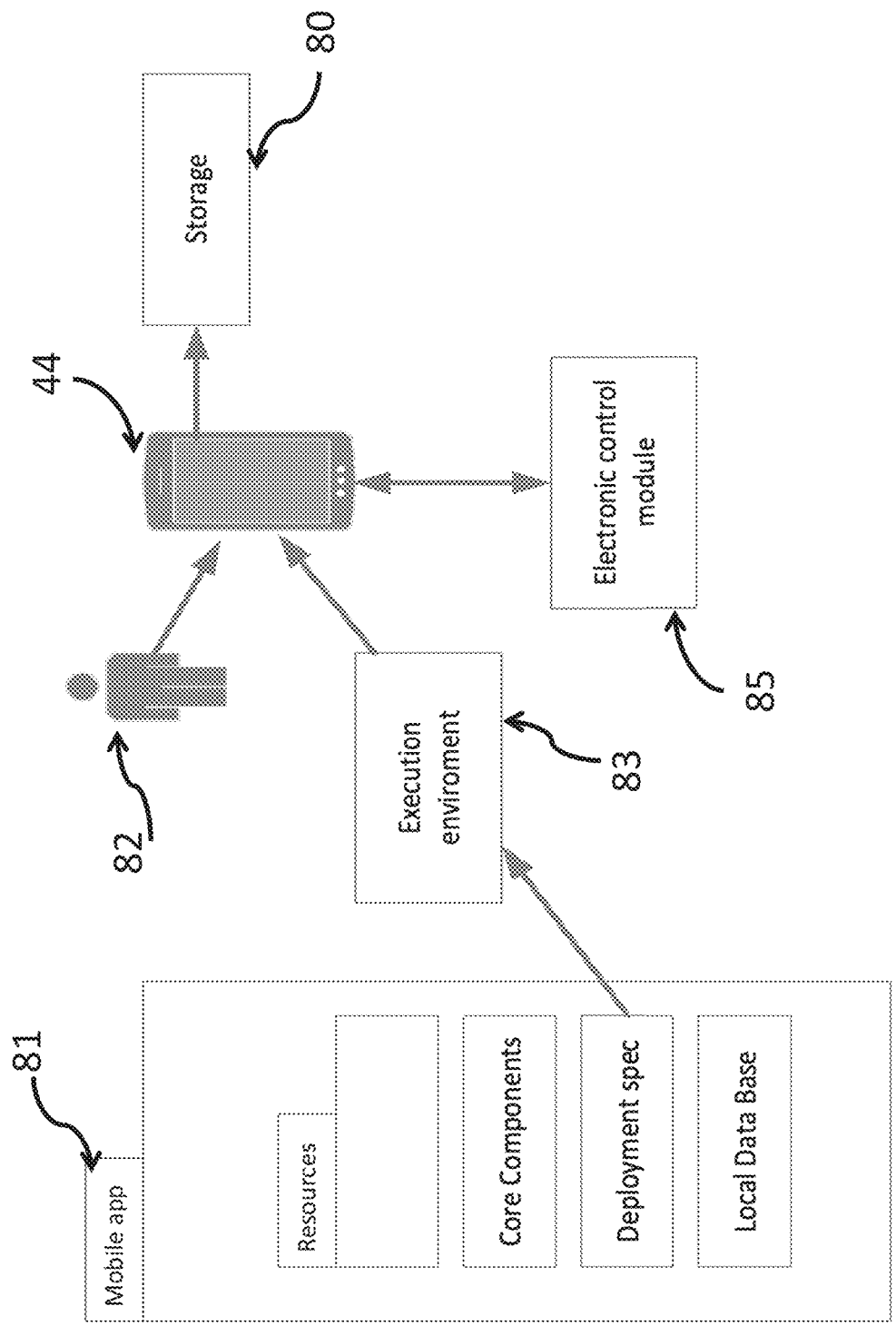
FIG. 16 illustrates a system deployment diagram.

FIG. 16 shows the deployment diagram of the application of the mobile device. This application works on an execution environment 83 such as Android Operating System. The user 82 accesses the mobile app 81 through a mobile device 44. The communication is established with the electronic control module 85. The user data profile is stored in a local database 80.

Figure 17:
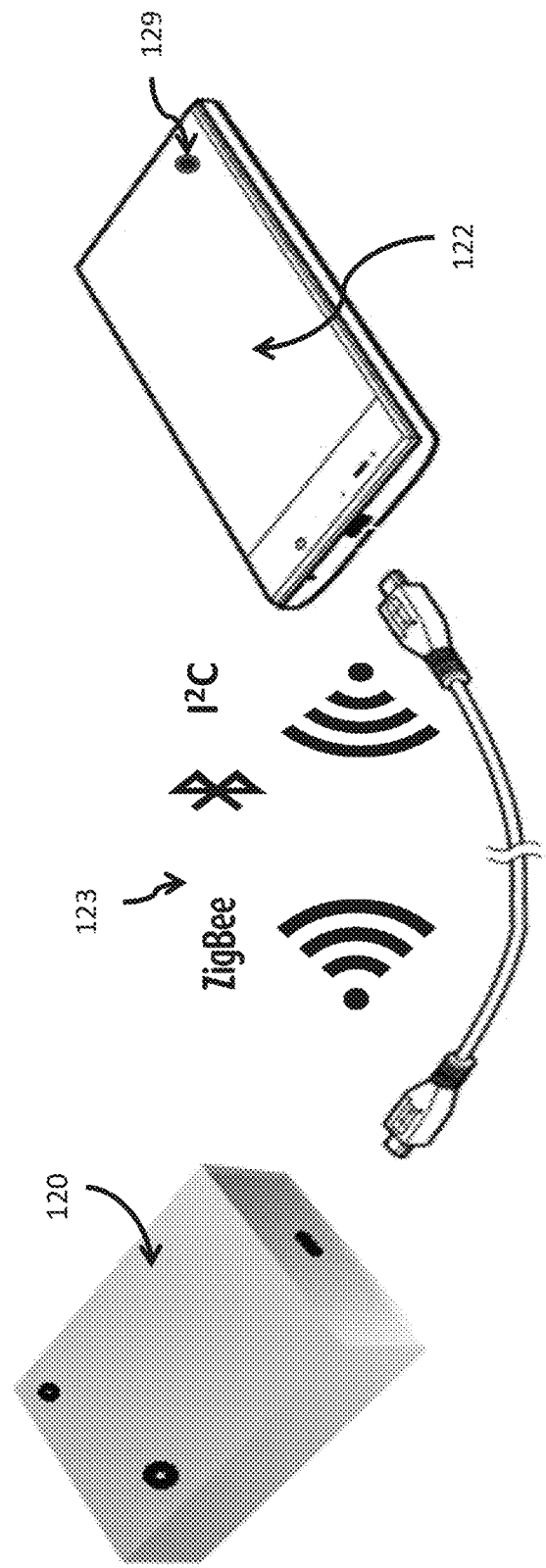
FIG. 17 is a schematic view of the system major components of a generic system for stimulation: mobile device, electrical stimulation device and their connection that may be used in accordance with the method of the present invention.

Referring to FIG. 17, an exemplary embodiment of any (not only salivary) electrical stimulation device that may be used in accordance with the method of the present invention where the user controls and programs the stimulation parameters and placement of the electrodes, using a mobile device 122 and its communication means 123, wired such as micro-USB or wireless such as Bluetooth. The mobile device camera 129 is used for the placement of the stimulating electrodes properly. The user uses mobile device input devices, such as touch screen, stylus, keyboard etc. to control the stimulation parameters and the placement of electrodes.

Figure 18:
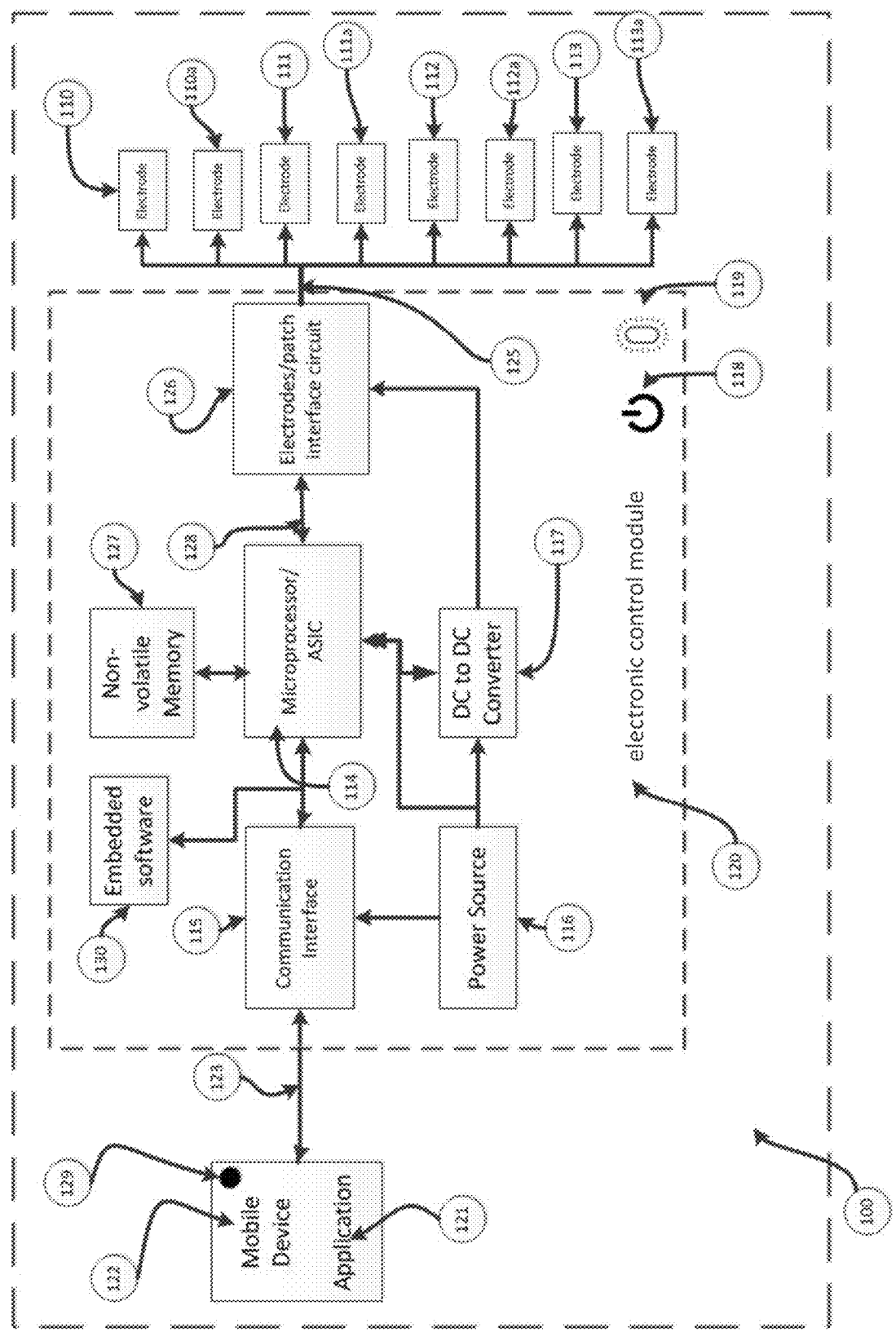
FIG. 18 is a block diagram of an electrical stimulation device that may be used in accordance with the method of the present invention.

Referring to FIG. 18, an exemplary schematic diagram of any salivary (not only parotid) electrical stimulation device that may be used in accordance with the method of the present invention is designated generally as reference numeral 100. The electronic stimulation system 100 generally comprises an electronic control module 120 with a plurality of outputs, which are connected to a plurality of output cables 125 and associated electrode pairs 110, 110a, 111, 111a, 112, 112a and 113, 113a.

Output cables 125 each comprise any suitable type of insulated conductive cable, such as a coaxial cable. Additional major components that are included, but not limited to, in the electronic control module 120 are: a power source 116, like a battery, a DC to DC converter 117 that steps up or down the voltage of the power source 116 to the requested output voltages at the electrodes pairs 110, 111, 112, and 113. The DC to DC output voltage is control by the microprocessor 114 and its embedded software 130. The voltages of the Dc to DC converter 117 are set in accordance to the programming of the user at the mobile device 122 and using the software application 121. The outputs of the DC to DC converter 117 feeds the electrodes/patch interface circuit 126, which includes drivers such as open collector transistors, or FETs transistors or similar circuitry. The electrodes/patch interface circuit 126 is controlled by the microprocessor I/O lines 128 that generated the proper stimulation signal to each channel, based on programmed and selected stimulation by the user at the mobile device 122.

The user defines all the stimulation parameters and downloads those parameters to the electronic control module 120 where the microprocessor 114 and its embedded software 130 translate the data to an accurate stimulation. The electronic control module 120 is a self-contained unit that includes a power source 116, microprocessor 114 and all other components as detailed in FIG. 7, to run the stimulation session without any connection or intervention of the mobile device 122.

The built-in microprocessor 114 and its embedded software 130 convert the stimulation parameters selected by the user at the mobile device and download them to the electronic control module 120 for an accurate stimulation, by each channel. The electronic control module 120 is a self-contained unit that includes, but not limited to, a DC to DC converter 117 for stepping up and down the voltage to the output and feeds the electrodes/patch interface circuit 126, a power source 116 microprocessor 114, communication interface 115 with the mobile device 122, and all other components as detailed in FIG. 7 to run the stimulation session without any connection or intervention of the mobile device 122. The electronic control module 120 is capable of operating independently, i.e. without a connection to the mobile device 122. Thus, it incorporates a power on/off switch 118 and a power on and other data indicators (like a LED or LCD) 119. Upon power on, the system will use the most updated programmed stimulation parameters. Those parameters as well as other data and software code may be stored in the non-volatile memory 127 that can be part of the microprocessor IC or in a separate IC.

The electronic control module 120 is connected to the mobile device 122 via a communication interface 115, which can be wired 123 such as USB, Micro USB I²C and the like, or wireless such as Bluetooth, ZigBee, and the like.

Camera 129 (front or rear) is part of the mobile device standard accessories and is controlled by its software 121 and operating system.

Figure 19:
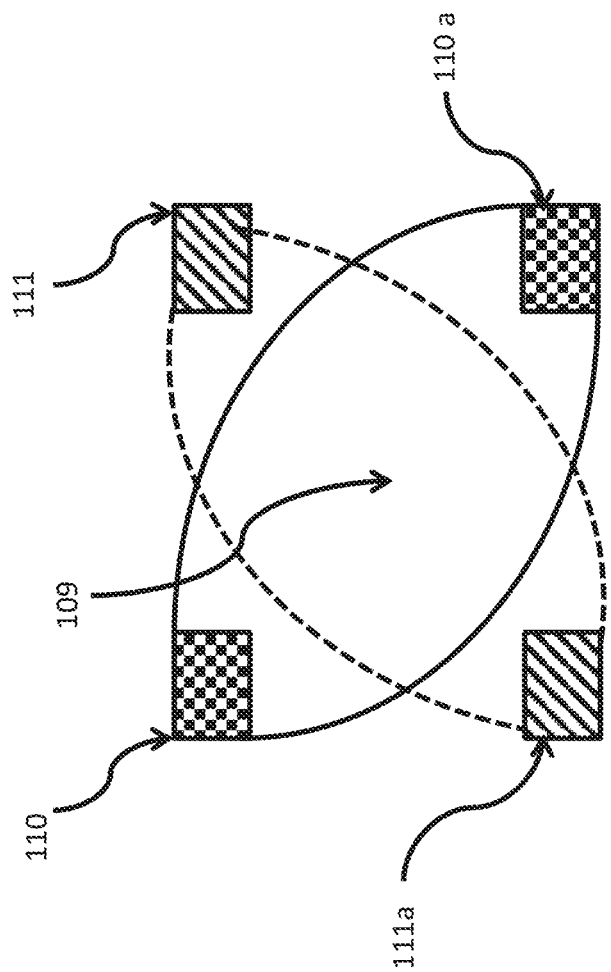
FIG. 19 is a diagram of Interferential Current (IFC) stimulation principle that may be used in accordance with the method of the present invention.

Referring to FIG. 19, the concept of Interferential Current (IFC) is demonstrated. As shown the electrodes pairs, 110/110a and 111/111a stimulations area cross each other and overlapped a region 109 where the two stimulation waves interference generate the stimulation at the tissue, which is the modulation of the frequencies of each channel, including the difference between each pair. As an example; electrodes pair 110/110a generates stimulation at carrier frequency of 4000 Hz and electrodes pairs 111/111a generate at 4100 Hz the difference of 100 Hz is the effective stimulation at the crossed region. It should be noted that also other frequencies are generated out of the interference of the two stimulation pairs, however, those are usually at higher frequencies and may, as the characteristic of the stimulation is very individual and not very well understood by the scientific community, also generate a stimulation of the salivary mechanism.

Figure 20:
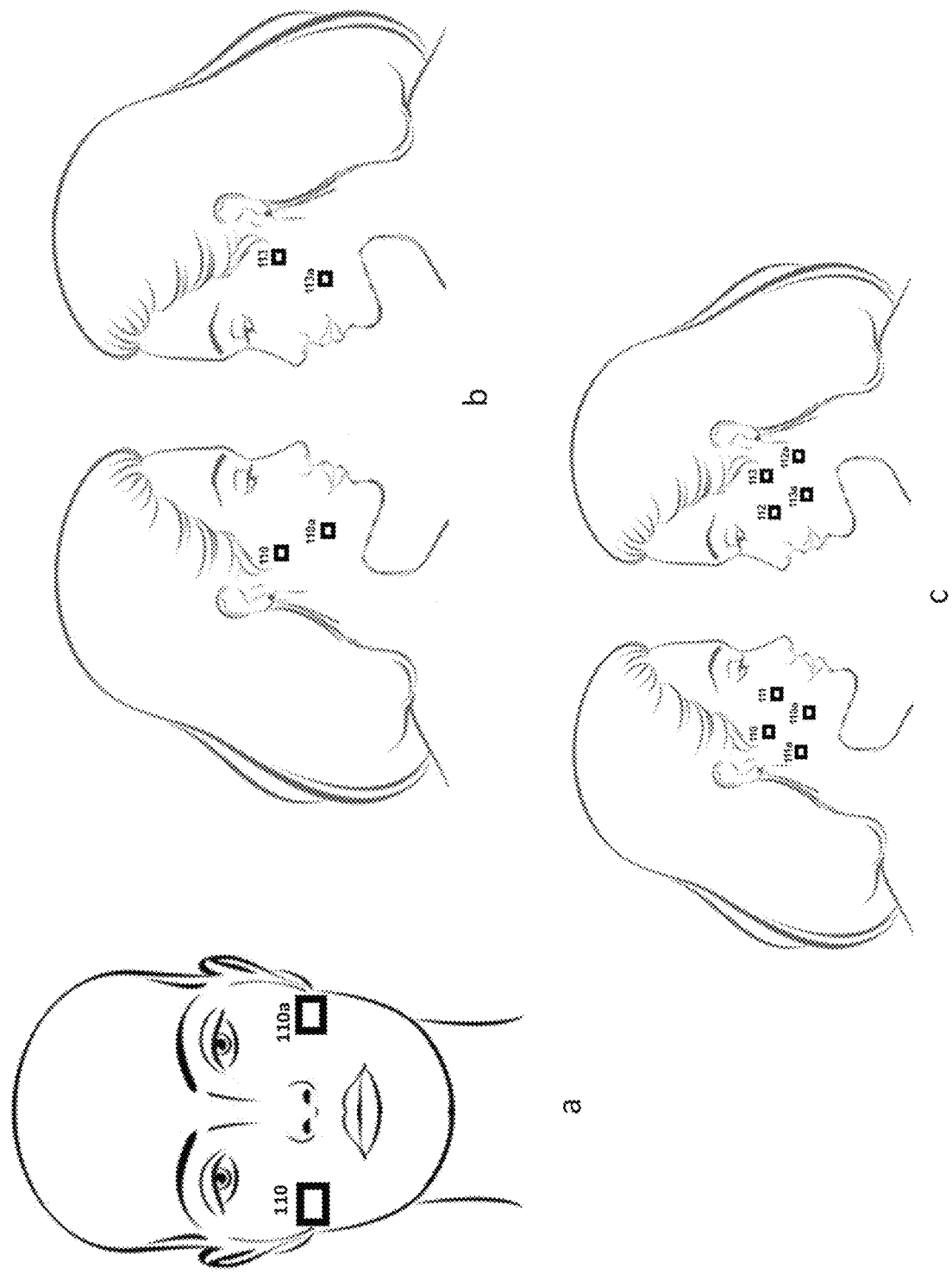
FIGS. 20a, b and c are optional placement of the stimulation electrodes aimed at stimulating the parotid glands that may be used in accordance with the method of the present invention.
Figure 21:
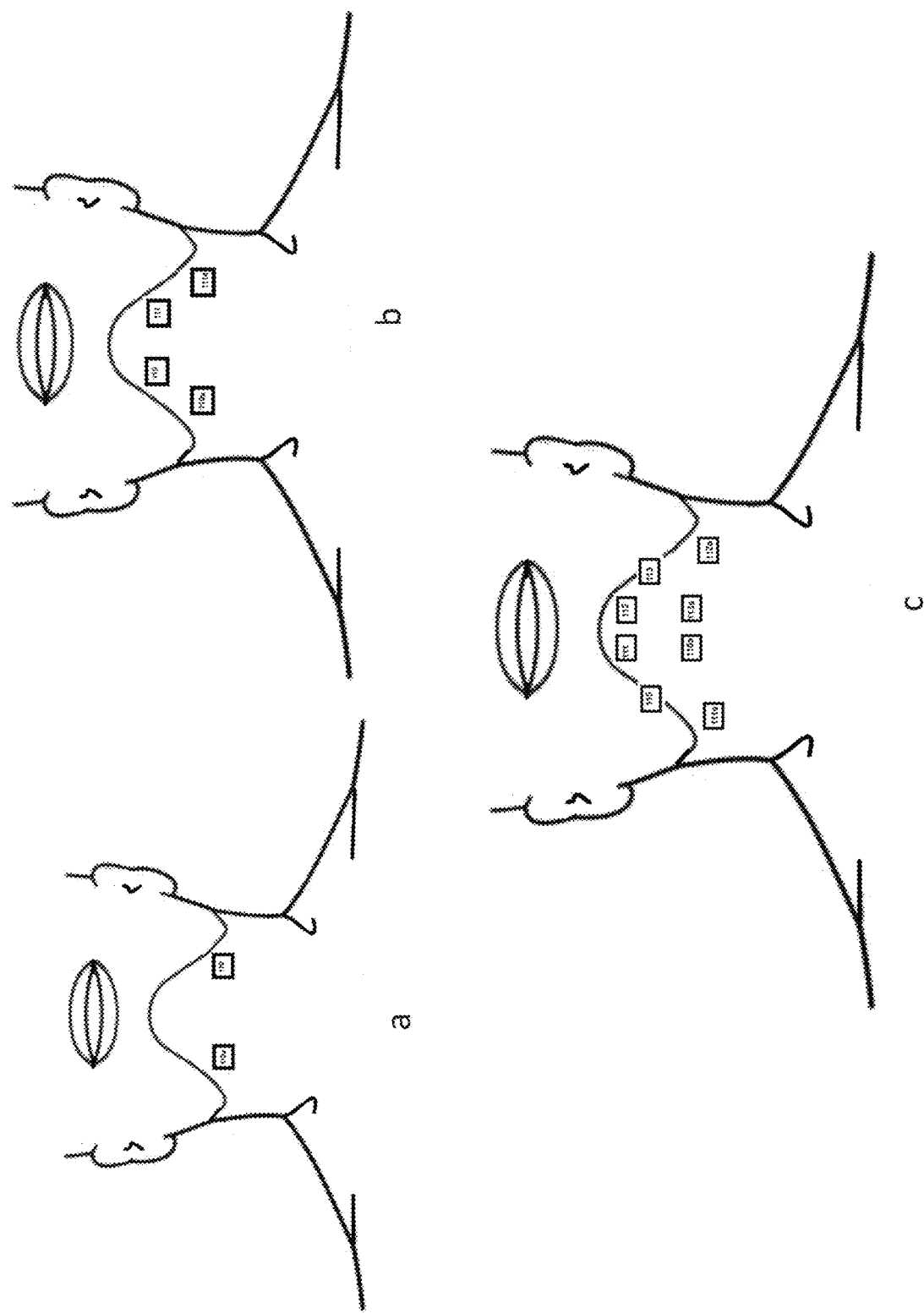
FIGS. 21a, b and c are optional placement of the stimulation electrodes aimed at stimulating the submandibular/sublingual glands that may be used in accordance with the method of the present invention.

Referring to FIG. 20, some of the anatomical regions to place the electrodes on the cheek in order to stimulate the parotid gland secretion are shown as follows: FIG. 20a, stimulation of the parotid glands using a non-IFC method with a single pair of electrodes (e.g., 110/110a, whereas electrode 110 is placed on the right parotid gland and 110a on the left parotid gland); FIG. 20b, stimulation of the parotid glands using a non-IFC method with one or two pairs of electrodes (e.g., 110/110a and/or 113/113a, whereas electrodes 110/110a are placed on the right parotid gland and/or 113/113a on the left parotid gland). The electrodes are placed on the skin covering the parotid gland and extending from the ear to the cheek, close or inside the ear; and FIG. 20c, using an IFC method with two and/or four pairs of electrodes (e.g., 110/110a and 111/111a on one side, and 112/112a and/or 113/113a on the other side, whereas electrodes 110/110a and 111/111a are placed on the right parotid gland and/or 112/112a and 113/113a on the left parotid gland). Referring to FIG. 21, some of the anatomical regions to place the electrodes on the anterior neck area in order to stimulate the submandibular/sublingual gland secretion are shown as follows: FIG. 21a, stimulation of the submandibular/sublingual glands using a non-IFC method with a single pair of electrodes (e.g., 110/110a, whereas electrode 110 is placed on the right submandibular/sublingual glands and 110a on the left submandibular/sublingual glands); FIG. 21b, stimulation of the submandibular/sublingual glands using a non-IFC method with one or two pairs of electrodes (e.g., 110/110a and/or 111/111a, whereas electrodes 110/110a are placed on the right submandibular/sublingual glands and/or 111/111a on the left submandibular/sublingual glands); and FIG. 21c, using an IFC method with two and/or four pairs of electrodes (e.g., 110/110a and 111/111a on one side, and 112/112a and/or 113/113a on the other side, whereas electrodes 110/110a and 111/111a are placed on the right submandibular/sublingual glands and/or 112/112a and 113/113a on the left submandibular/sublingual glands).

Figure 22:
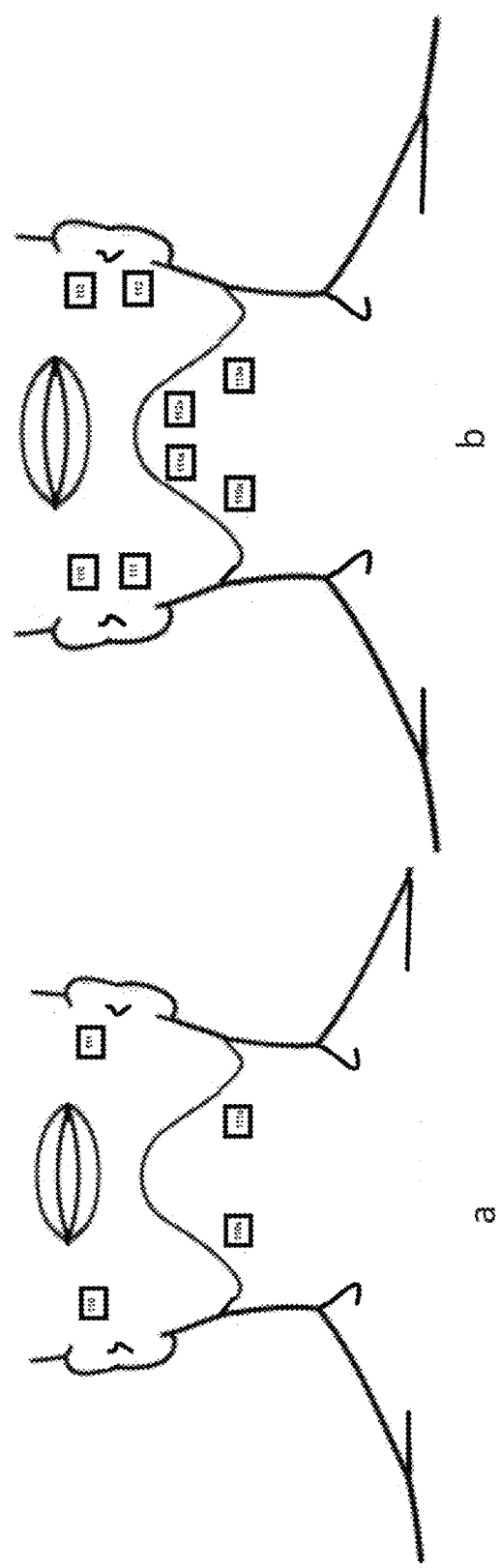
FIGS. 22a and b are optional placement of the stimulation electrodes aimed at jointly stimulating the parotid and submandibular/sublingual glands that may be used in accordance with the method of the present invention.

Referring to FIG. 22, some of the anatomical regions to place the electrodes on the cheek and the anterior neck area in order to stimulate jointly the parotid and submandibular/sublingual gland secretion are shown as follows: FIG. 22a, stimulation of the right parotid and submandibular/sublingual glands using a non-IFC method with one or two pairs of electrodes (e.g., 110/110a and/or 111/111a, whereas electrodes 110 are placed on the right parotid gland and electrodes 110a are placed on the right submandibular/sublingual glands and/or 111 are placed on the left parotid gland and electrodes 111a are placed on the left submandibular/sublingual glands); and FIG. 22b, using an IFC method with two and/or four pairs of electrodes (e.g., 110/110a and 111/111a on one side, and 112/112a and/or 113/113a on the other side, whereas electrodes 110 and 111 are placed on the right parotid glands and 110a and 111a are placed on the right submandibular/sublingual glands and/or electrodes 112 and 113 are placed on the left parotid gland and electrodes 112a and 113a are placed on the left submandibular/sublingual glands).

It should be noted that the numbers of the electrode pairs can vary and each electrode pairs can be placed at any selected location and be programmed accordingly. The figures are for example manner only.

Figure 23:
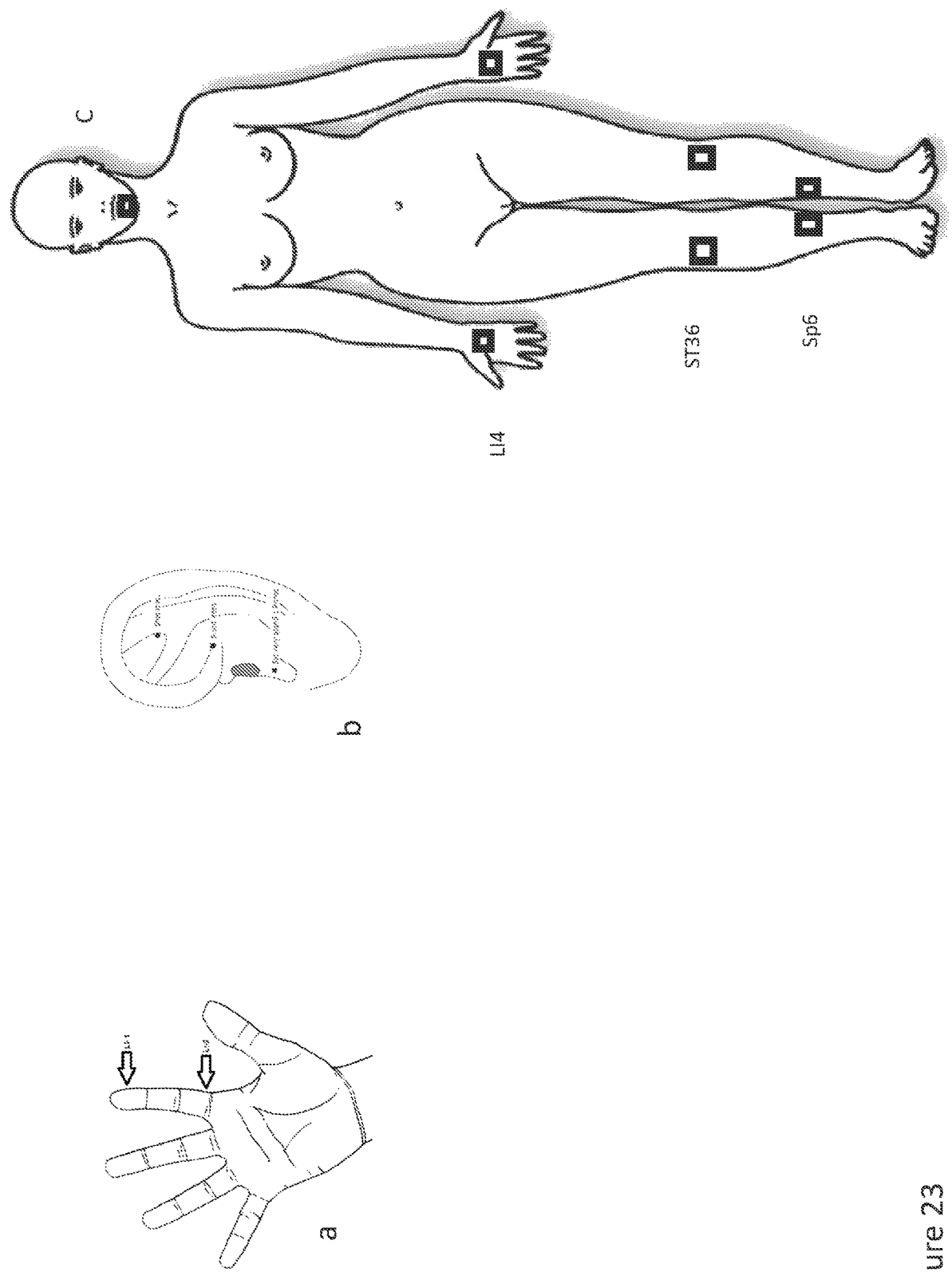
FIGS. 23a, b and c are few of optional placement of the stimulation electrodes, known in acupuncture, that may be used in accordance with the method of the present invention.

Referring to FIG. 23, some of the anatomical regions to place the electrodes on the known anatomical stimulation regions for saliva stimulation and dry mouth treatment, using acupuncture known stimulation points, are shown in FIG. 23a (on the hands), FIG. 23b (on the ears), and FIG. 23c (on different other body areas).

Figure 24:
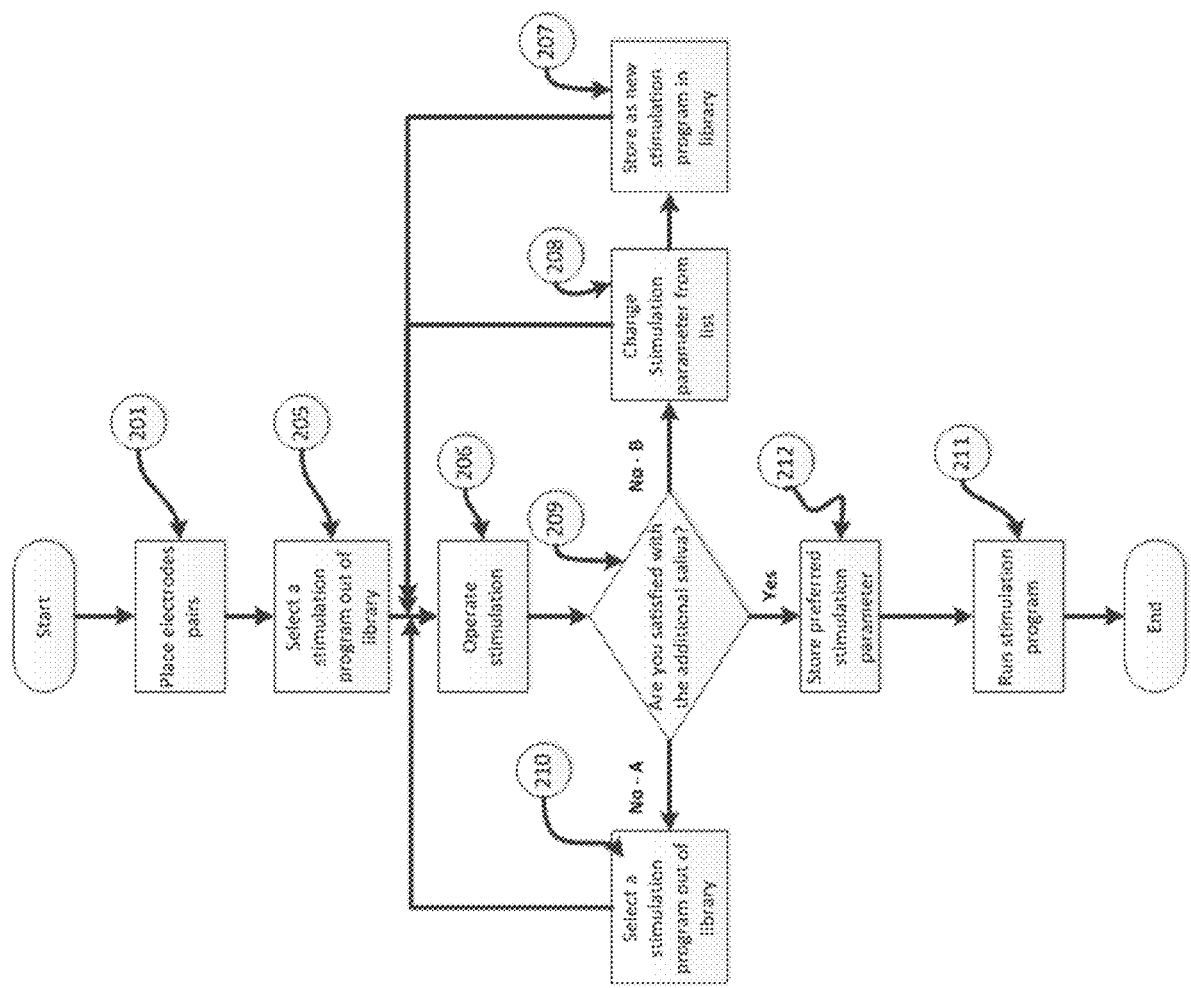
FIG. 24 is a block diagram of method and control steps the user takes in using the mobile device and its software selection of the preferred stimulation parameters only.

Referring to FIG. 24, the closed loop and the bio-feedback method of selecting the preferred stimulation parameters and anatomical regions is demonstrated. As shown the user places the electrode pairs at his/her preferred anatomical regions 201 (based on suggested sites by the user manual), then he/she selects the set of parameters 205 (based on suggested sites by the user manual) to start the stimulation with. The stimulation starts 206, then, based on his/her subjective feeling 209 i.e. as asked by the system's display or by a vocal notification ("is your xerostomia—dry mouth sensation—improved or not?") If the user is satisfied, he/she can at will, store the preferred electrode location and electrical parameters 212 under a unique designated name in the mobile device memory, to be used in later sessions and can continues with the stimulation 211 itself. If the user is not happy with the results, he/she can either select another set from of the library 210 or set new parameters individually 208 and store them in the library 207 and repeat this closed loop process until they are satisfied with the results 211.

The user can select each parameter individually, then if the user is satisfied (either by the short or long effect of the stimulation) he/she stores all those selected stimulation parameters under a unique name (say; best_saliva_after_meal.cmv) and for next time, instead of setting each parameter, reload this file, that loads the preferred parameters.

Figure 25:
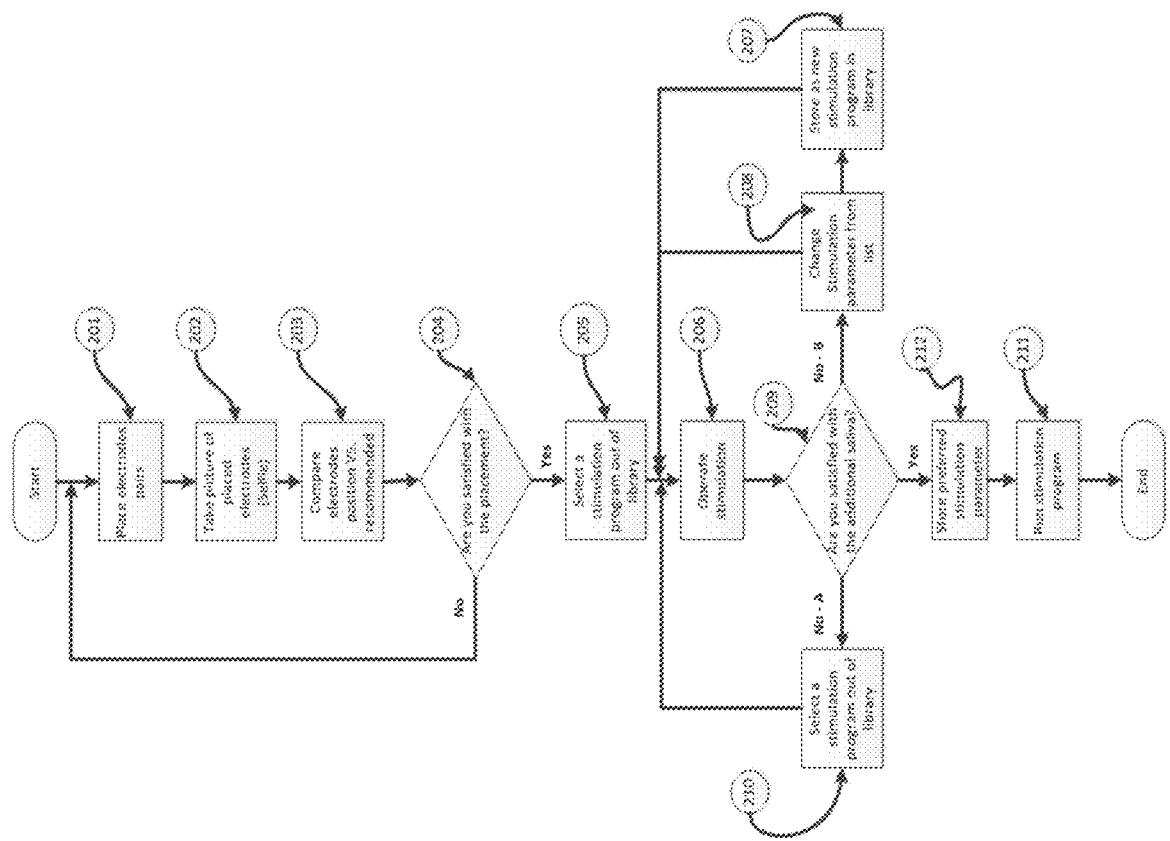
FIG. 25 is a block diagram of method and control steps the user takes in using the mobile device and its software for placement of electrodes and selection of the preferred stimulation parameters.

Referring to FIG. 25, it is similar to FIG. 24 but with a preliminary setting and placement of the electrodes using the mobile device camera and selfie mode to close the loop on correct placement of the electrodes. The user places the electrodes 201 and takes a picture 202 comparing the picture to a picture in the user's manual, for the recommended placement 203 or to what he/she prefers, then if they are satisfied with the placement 204, they continue selecting the stimulation parameters as described in FIG. 24, or re-position the electrodes and repeat the process until they are satisfied, thus closing the loop with their bio feedback.

Figure 26:
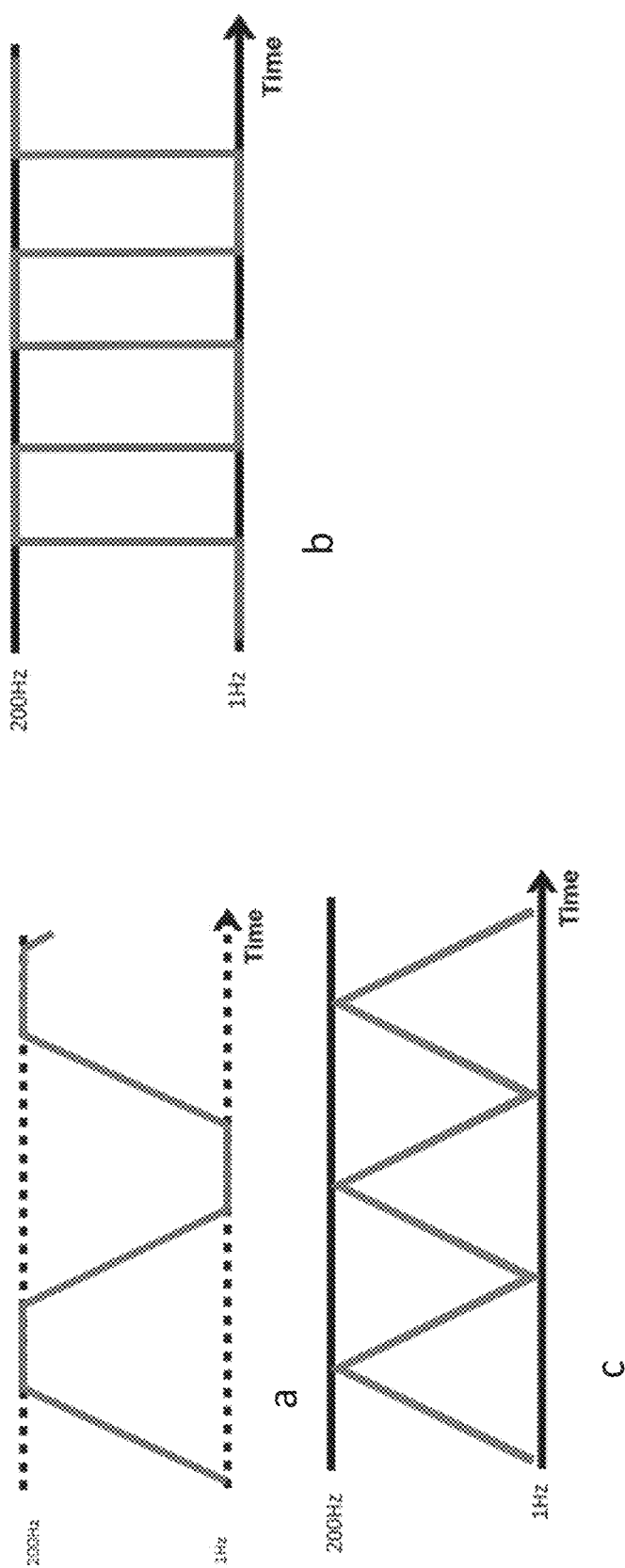
FIGS. 26a, b and c are schematic presentation of optional stimulation frequency shift.

Referring to FIG. 26, it shows schematically few examples of frequency swift patterns, trapezoid FIG. 26a rectangular FIG. 26b or triangular in FIG. 26c. Other patterns can be realized like randomly shifting the frequencies, sinusoidal and the like. Swifting the carrier frequency can improve the stimulation effect by generating an alternating stimulation.

Figure 27:
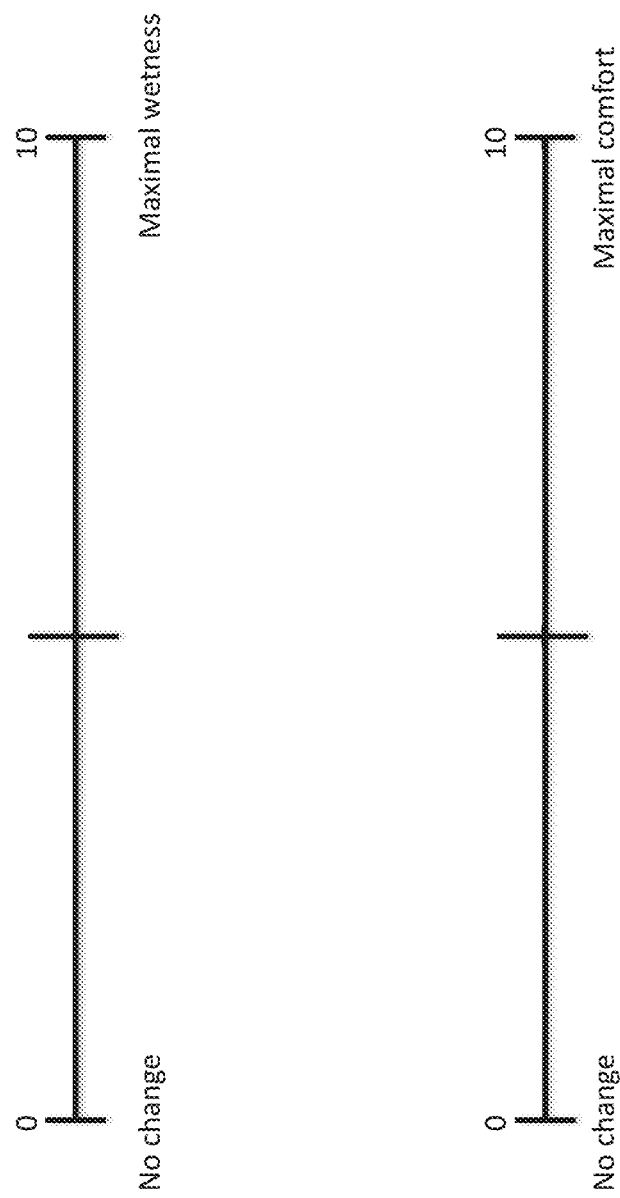
FIG. 27 shows the Visual Analogue Scale (VAS) used for the experiment.

Referring to FIG. 27, it shows schematically the VAS Value Analogue Scale.

Figure 28:
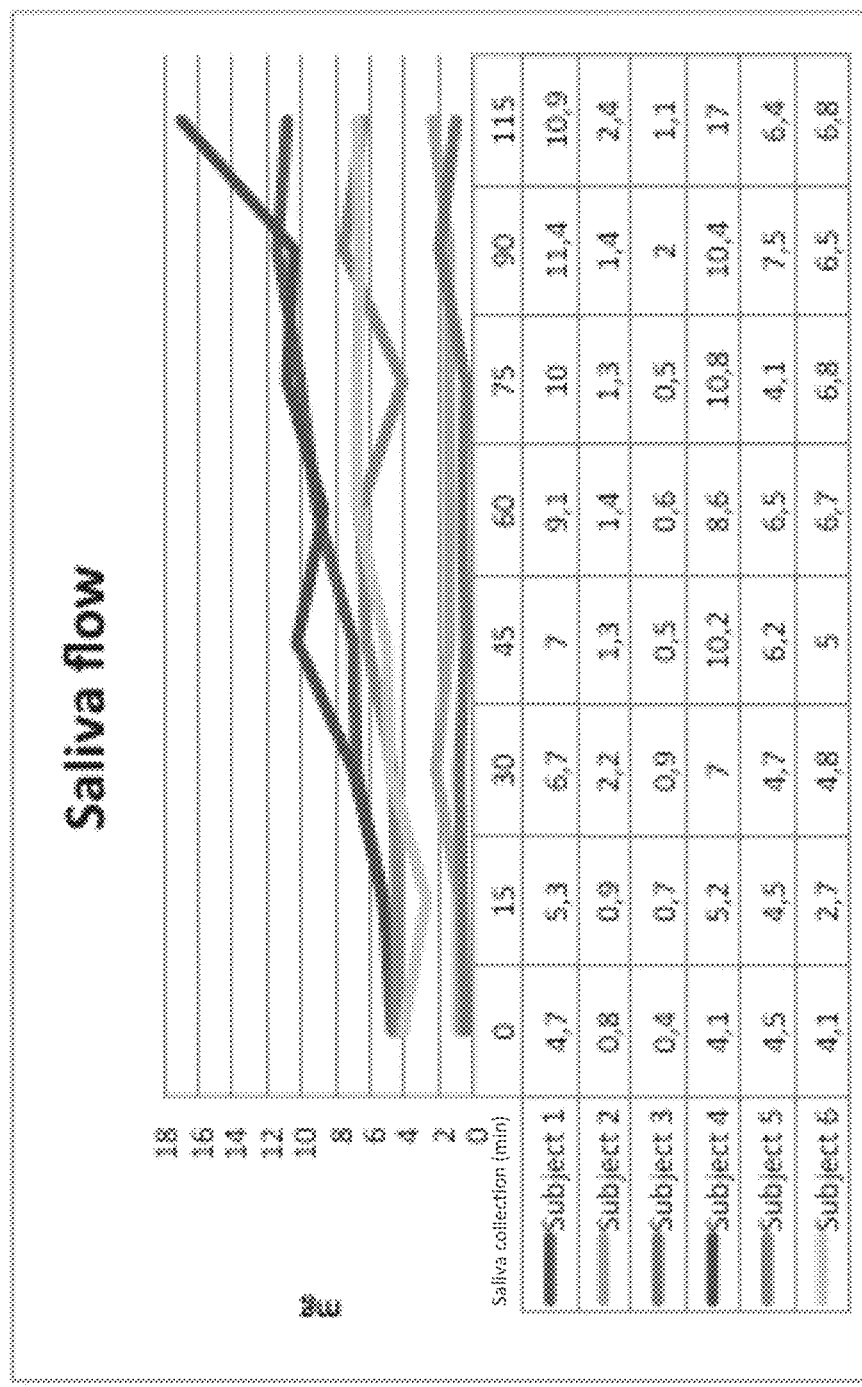
FIG. 28 shows the graph and data obtained as result of the experiment.

Referring to FIG. 28, it shows the increase of salivary flow at the experiment conducted by the system.

Referring to FIG. 29, it shows the symptomatic improvement obtained in the clinical trial.

Referring to FIG. 30, it shows a side view of a potential user face. As shown, the system is hinged on elastic arms 1a an arch like placed on top of the head (like a standard headset) or on the back head (similar to a "sport" headset configuration). The box with the electronic control module 2 is attached to the elastic arms 1a. An ear-plug 4 positions the system in a fixed location and anchors the stimulating module. The ear-plug 4 serves as a reference and pivot point to the adjustment of the stimulating module. An elastic bar 300 made of stainless steel, titanium, nitinol, composite material or any combination thereof, connects the stimulating plate 5 with the stimulating electrodes 6 to the electronic control module inside its box 2 via the elastic arm 1a. It is connected by wires or a flexible PCB. The elastic bar 300 is applying pressure that pushes the stimulating plate 5 toward the user's skin, to improve the electrodes contact with the skin. The stimulating electrodes 6 can be arranged on the plate 5 in a number of different placement configurations, have varying thickness, shape, materials (gold, brass, copper, stainless steel and other conducting, bio-compatible materials). The elastic bar 300 uses the ear-plug as a pivotal point and allows adjustment of the stimulating module (see also FIG. 4). Sliding the stimulating module along the elastic bar 300 allows also adjustment of the stimulating module in a preferred location (i.e., more neuro-sensitive) to achieve better stimulation.

Figure 31:
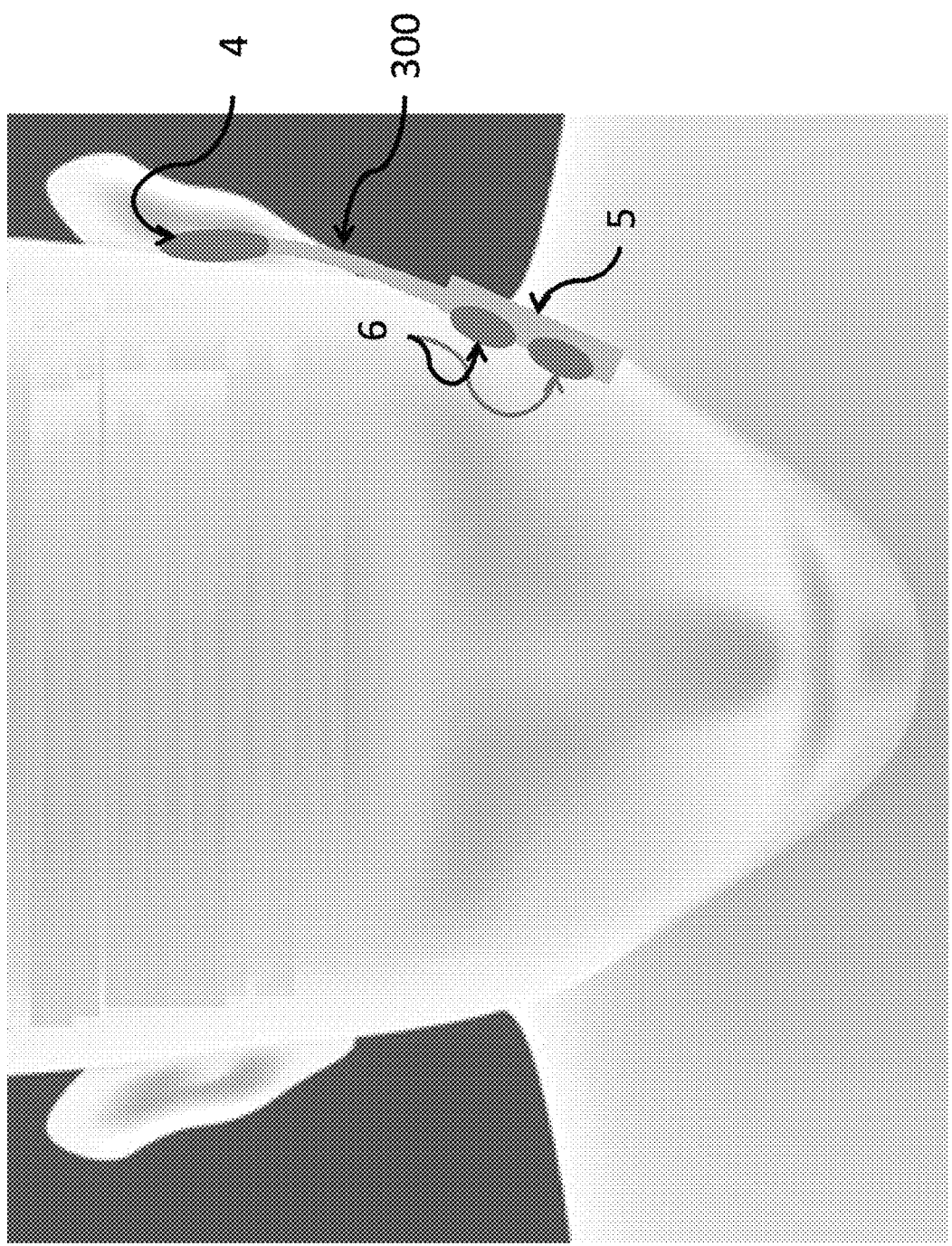
FIG. 31 depicts an upper view of a user wearing the headset and in particular the stimulating module.

Referring to FIG. 31, an isometric view of a typical use. The ear-plug 4 connected to an elastic bar 300 that is bent and designed to push the stimulating plate 5 toward the user's skin. The stimulating electrodes 6 then are in contact with the user's skin. The stimulating electrodes 6 are connected by wires or PCB, or any combination thereof, via the elastic arms to the electronic control module (FIG. 30).

Mechanism of Action

Starting from FIG. 18, the electrical stimulation system 100 includes an electronic control module 120 connected to one or more channels of electrodes 110, 110*a*, 111, 111*a*, 112, 112*a* and 113, 113*a*, such as transcutaneous or percutaneous electrodes and a connection to an off the self-mobile device 122 connected 123 via USB cable of wireless connection such as Bluetooth, Low-power Bluetooth, ZigBee, I²C and the like (also shown in FIG. 17). Each channel comprises two electrodes (i.e., a relative positive electrode and a relative negative electrode), wherein the electrodes are positioned with an electrical contact with tissue of a target region of the patient to stimulate saliva secretion from salivary glands. The electronic control module 120 applies a series of electrical pulses to the patient through one or more channels of electrodes in accordance with a selected procedure for treating dry mouth. Pulse width may vary from 50 microsec to 5 mSec, 250 micro-second or 1 mSecond. The selection of a procedure and its parameters is performed via a mobile device software application 121. The user selects a specific procedure out of predefined procedures and can, at will, using the mobile device inputs (touchscreen, stylus, keyboard, mouse), also alter key parameters of the stimulation procedure, such as; voltage, current, stimulation time, stimulation pattern, pulse shape, pulse train parameters, main stimulation frequency, delta frequency of the secondary stimulation frequency (IFC method), frequency shift pattern waveform, which may be, for example, trapezoid (FIG. 26*a*), asymmetric square (FIG. 26*b*), triangle (FIG. 26*c*), symmetric, square, sinusoidal, secondary stimulation frequency limits (upper frequency and lower frequency). The selected stimulation parameters are downloaded to the electronic control module and are used to generate the required stimulation. Using the mobile device camera 129 ("Selfie" method) the user can position and compare his/her positioning of the electrodes on one's face and compare it with the recommended positioning of the electrodes, given in the user's guide at the mobile device.

As shown in FIG. 20 and FIG. 21, in the present invention, the electrodes are preferably placed on the patient in a manner that they stimulate the salivary glands and/or the salivary related nerves (lingual) and/or salivary sensory mechanism and/or the salivary center in the brain. Thus, for example, in the present invention, one preferred placement is one electrode at the right-anterior neck region or right-posterior cheek region of the patient and the other electrode at the opposite (left) site. Additional preferred placement of the electrodes could follow the traditional Chinese medicine, such as but not limited to acupuncture and electro-acupuncture, known local points are (only few are shown in FIG. 23) including: Juliao ST-3, Daying ST-5, Jiache ST-6, Xiaguan ST-7, Tianrong SI-17, Futu L.I.-18, Yifeng SJ-17 and Baihui DU-20, and distal points including Shenmen HE-7, Neiguan P-6, LI-1, LI-2, Sanjian L.I.-3, Hegu L.I.-4, Quchi L.I.-11, Waiguan SJ-5, Zusanli ST-36, Sanyinjiao SP-6, Zulinqi GB41, Taichong LIV-3, Taixi KID-3, Shuiquan KID-5, Point zero, Salivary gland 2 prime (FIG. 23).

The user selects the mode of operation and its parameters. Those selected parameters are sent to the electronic control module 120 via wired or wireless communication 123 and are used by the electronic control module processor embedded software 130 in generation of the desired stimulation pattern.

The Selfie method (a photograph that one takes of oneself, typically with a smartphone or webcam and that can be shared via social media) may be used to validate proper positioning of the electrodes. Proper positioning is compared with the recommendation given by the mobile device application and presented to the user on the mobile device screen. This method allows closing the loop of positioning the electrodes in the correct places.

The series of electrical pulses applied to the one or more channels of stimulating electrodes 6 may comprise a variety of different types of pulse train patterns. For example, a plurality of cycles of a biphasic sequential or overlapping pulse train pattern may be used, in which a first phase of electrical pulses is applied to a first channel of electrodes and a second phase of electrical pulses is applied to a second channel of electrodes. Using the biphasic sequential pulse train pattern, the second phase of electrical pulses commences after termination of the first phase of electrical pulses such that there is a time delay there between. Using the biphasic overlapping pulse train pattern, the second phase of electrical pulses commences before termination of the first phase of electrical pulses such that there is an overlap there between.

In another example, a plurality of cycles of a triphasic sequential or overlapping pulse train pattern may be used, in which a first phase of electrical pulses is applied to a first channel of electrodes, a second phase of electrical pulses is applied to a second channel of electrodes, and a third phase of electrical pulses is applied to the first channel of electrodes. Using the triphasic sequential pulse train pattern, the second phase of electrical pulses commences after termination of the first phase of electrical pulses such that there is a time delay there between and, similarly, the third phase of electrical pulses commences after termination of the second phase of electrical pulses such that there is a time delay there between. Using the triphasic overlapping pulse train pattern, the second phase of electrical pulses commences before termination of the first phase of electrical pulses such that there is an overlap there between and, similarly, the third phase of electrical pulses commences before termination of the second phase of electrical pulses such that there is an overlap there between.

In yet another example, the series of electrical pulses comprises a functional pulse train pattern applied to one or more channels of electrodes. In yet another example a jitter is used in the generation of pulse train effectively act like continuous change of the stimulation frequency between per-selected boundaries. In a further example, the series of electrical pulses comprises a pulse train pattern applied to one or more channels of electrodes, wherein the individual electrical pulses are generated at a frequency different from the main frequency between 0.1 Hz and 200 Hz, approximately 1 Hz, 5 Hz, 20 Hz, 30 Hz, 50 Hz, 100 Hz, 5 Hz, 50 Hz, to selectively generate the relative selective production neurotransmitters and modulators based on the frequency selected. Stimulation at specific frequencies is believed to have beneficial effects in the treatment of dry mouth due to the normalization of hyperactive sensory inputs (which play a role in the re-education of the central salivary center generators).

Alternatively, a frequency-sequenced pulse burst train pattern may be applied to one or more channels of electrodes, wherein different sequences of modulated electrical pulses are generated at different burst frequencies. The different burst frequencies may be selected so as to generate the simultaneous production of natural saliva from multiple glands, the respective sequences, which is believed to have beneficial effects in the treatment of dry mouth due to imitation of foreign body in the mouth and triggering the sensory inputs (which play a role in the stimulation of saliva secretion).

Results of Tests

This example presents the efficacy of the salivary bilateral parotid gland transcutaneous electro-stimulator, which was manufactured by a method mentioned herein. Saliva samples were collected in a quiet area, after two hours without any stimulus (food, drugs, chewing gum, smoking, brushing, rinses, alcoholic beverages). They were asked not to consume drugs one day before the test. The subjects were asked to wash their mouth with water before starting the test. They were then asked to sit quietly with the eyes open and the head slightly bent forward, without swallowing, talking, and without making any oral movements or chewing and squeezing the saliva that accumulates on the floor of the mouth. This pilot experiment in six salivary normal patients using the electro-stimulating device was designed as follows:

1-Saliva was collected in each subject at the beginning of the experiment at 10:00 am and thereafter at 15 minutes intervals during a total of 115 minutes time period. The collections at minutes 0 and 15 minutes were under no stimulation while those at the remaining 100 minutes were performed during the parotid electrical stimulation.

2-Saliva was collected into a disposable pre-weighted cup with an electronic milligram scale.

3-The device was switched on with electrodes on place (FIG. 4) after completion of the first 15 minutes without any stimulation.

4-Pre-wetting the parotid overlying skin with a conductive gel preceded the placement of the electrodes before the start of the stimulation. The intensity of the stimulation device varied between subjects (2.8-3.8 V) selected by each volunteer according to their comfort sensation. The frequency of the stimulation was set to 160 Hz. Modes of pulse width stimulation varied between constant and burst (with 260ms) and modulated (increasingly 18.3, 48.8, 79.3, 109.8, 140.3, 170.8, 201.3, 231.8, 262.3) with one minute for intervals between them.

5-Finally patients were asked at the end of the test to rate their oral wetness sensation and comfort sensation using a separate Visual Analogue Scale (VAS) for each measure. The VAS scales were rated "0-10", meaning VAS "0" no change and "10" the maximal wetness sensation or comfort sensation, as shown in FIG. 27.

The results on salivary flow measured as weight of collected saliva is represented in the graph of FIG. 28. The graph shows an increasing and fluctuating saliva flow (average 7.4 mg at minute 115), compared to the initial saliva flow without the stimulating device (average 3.1 mg).

Subject reported changes in VAS wetness and comfort levels are shown on FIG. 29. In general, all subjects reported higher wetness sensation after the use of the device with the smallest wetness and comfort changes in subject 6 and the highest in subjects 1 and 3. Excepting subject 3, discomfort was reported in all subjects at the beginning of the stimulation but disappeared after 30 minutes.

The following conclusions can be drawn: there is an improvement in salivary secretion as measured during 115 minutes; and the salivary parotid glands have a good response to electro-stimulation.

It should be understood, of course, that the foregoing relates to exemplary embodiments of the invention and that modifications may be made without departing from the spirit and scope of the invention as set forth in the following claims.

What is claimed is:

1. A biofeedback system for self-treating dry mouth using an electrical stimulation, wherein the biofeedback system enables adjustments to a location and a parameter of the electrical stimulation based on biofeedback to an effect on salivary secretion imparted by the location and the parameter of the electrical stimulation, the biofeedback system comprising:
    a mechanical biofeedback component, comprising:
        an anchor element dimensioned and shaped to securely nest in an ear canal of a human user, wherein the anchor element provides a pivot point;
        a proximal end of a bar directly connected to the pivot point to rotate about the anchor element;
        a stimulating plate connected to a distal end of the bar; and
        a control module container directly interconnected to the anchor element by way of an elastic arm so that the control module container is configured to be movable between adjacent a lower neck and a top portion of a head of the human user; and
    an electronic biofeedback component, comprising:
        one or more electrode pairs connected to the stimulating plate so that of the one or more electrode pairs is selectively pivotable to electrically engages one of a plurality of auriculo-temporal nerves of a parotid gland of the human user upon receiving biofeedback comprising the effect on salivary secretion based on, in part, said electrical engagement; and
        a control module housed in the control module container, wherein the control module is operatively associated with each electrode of the one or more electrode pairs, wherein the control module is configured to selectively deliver, through each electrode, one of a plurality of salivary gland stimulation parameters upon receiving said biofeedback further comprising, in part, said salivary gland stimulation parameters; and
        a memory device coupled to the control module, wherein the memory device has a library configured to retrievable store salivary gland stimulation parameters and electrode salivary gland placement locations comprising a plurality of auriculo-temporal nerves of the parotid gland,
    whereby future self-treatment of dry mouth is facilitated.

2. The biofeedback system of claim 1, wherein the bar is spring- biased to selectively urge the one or more electrode pairs against said parotid gland.

3. The biofeedback system of claim 2, wherein the anchor element has a canal through which the bar is slidably connected, whereby the stimulating plate extends adjacent to a posterior cheek of the human user.

4. The biofeedback system of claim 3, wherein the control module is configured to selectively control power delivered to each electrode pair.

5. The biofeedback system of claim 4, further comprising a software application loaded on the control module for setting the stimulation parameters further defining said selective control of power.

6. The biofeedback system of claim 5, wherein the software application is configured to represent captured images of each of the electrode pairs electrically engaging one or more parotid glands for guiding the human user in said electrical engagement.

7. The biofeedback system of claim 6, wherein the control module container provides buttons for selecting the salivary gland simulation parameters.

8. The biofeedback system of claim 7, wherein the control module container comprises a display for representing said captured images.

9. The biofeedback system of claim 5, wherein the stimulation parameters are a function of an interferential current.

10. The biofeedback system of claim 5, further comprising electrical connections passing through the elastic arm between the control module and each pair of electrodes.

11. A method for treating dry mouth using electrical stimulation of auriculo-temporal nerves of a parotid gland, using the biofeedback system of claim 10, the method comprising:
  initially placing the one or more electrode pairs at one or more preliminary electrode salivary gland placement locations based on data retrieved by the library;
  initially selecting a sct of preliminary salivary gland stimulation parameters based on the library;
  in response to said biofeedback, moving the one or more electrode pairs to another one or more electrode salivary gland placement locations through pivoting the stimulating plate about the pivot point while the anchoring element is nested in said ear canal; and
  storing the preliminary electrode salivary gland placement locations, the preliminary salivary gland stimulation parameters, and said biofeedback under a unique designated name in the library.

12. The method of claim 11, wherein in response to said biofeedback, selecting other salivary gland stimulation parameters.

13. The biofeedback system of claim 1, wherein the anchoring element is substantially cylindrical in shape, wherein the anchoring element has a longitudinal length substantially greater than a diameter thereof.

14. The biofeedback system of claim 1, wherein the one or more electrode pairs are two electrode pairs, wherein one electrode pair is adjacent to a right parotid gland and the other electrode pair is adjacent to a left parotid gland.

15. The biofeedback system of claim 14, wherein the control module is configured to generate a carrier frequency difference of approximate 5 100 Hz between each electrode pair, whereby an effective stimulation is provided between an associated crossed region of the parotid gland.

16. The biofeedback system of claim 15, wherein the carrier frequency difference includes a biphasic series of electrical pulses.

* * * * *